US010433539B2

(12) United States Patent
White et al.

(10) Patent No.: US 10,433,539 B2
(45) Date of Patent: *Oct. 8, 2019

(54) COMPOSITION AND SOLUTION WITH CONTROLLED CALCIUM ION LEVEL, AND RELATED METHOD AND USE FOR REPERFUSION

(71) Applicant: TEVOSOL, INC., Edmonton (CA)

(72) Inventors: Christopher White, Edmonton (CA); Darren Freed, Edmonton (CA); Larry Hryshko, Edmonton (CA)

(73) Assignee: TEVOSOL, INC., Edmonton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/521,484

(22) PCT Filed: Oct. 23, 2015

(86) PCT No.: PCT/CA2015/051084
§ 371 (c)(1),
(2) Date: Apr. 24, 2017

(87) PCT Pub. No.: WO2016/061700
PCT Pub. Date: Apr. 28, 2016

(65) Prior Publication Data
US 2018/0192640 A1 Jul. 12, 2018

Related U.S. Application Data

(63) Continuation-in-part of application No. 15/302,593, filed as application No. PCT/CA2015/050297 on Apr. 10, 2015, now Pat. No. 10,327,441.

(60) Provisional application No. 62/068,524, filed on Oct. 24, 2014, provisional application No. 61/978,132, filed on Apr. 10, 2014.

(30) Foreign Application Priority Data

Apr. 10, 2015 (CA) .................. PCT/CA2015/050297

(51) Int. Cl.
A61K 31/167 (2006.01)
A01N 1/02 (2006.01)

(52) U.S. Cl.
CPC .......... A01N 1/0226 (2013.01); A61K 31/167 (2013.01)

(58) Field of Classification Search
CPC ..... A61K 38/33; A61K 31/167; A01N 1/0226
See application file for complete search history.

(56) References Cited

U.S. PATENT DOCUMENTS

| 5,405,742 A | 4/1995 | Taylor |
| 5,407,793 A | 4/1995 | Del Nido et al. |
| 6,524,785 B1 | 2/2003 | Cozzone et al. |
| 2003/0124503 A1 | 7/2003 | Olivencia-Yurvati et al. |
| 2005/0202394 A1 | 9/2005 | Dobson |
| 2006/0034941 A1* | 2/2006 | Dobson ................ A61K 31/167 424/608 |
| 2012/0077771 A1 | 3/2012 | Fallouh |
| 2014/0011745 A1 | 1/2014 | Dobson |

FOREIGN PATENT DOCUMENTS

WO 01/01774 A1 1/2001

OTHER PUBLICATIONS

U.S. Appl. No. 15/302,593.*
Examination Report No. 1 dated May 7, 2018 in related Australian Patent Application No. 2015336862.
Restriction Requirement dated Apr. 17, 2018 in related U.S. Appl. No. 15/302,593.
Jakobsen, et al., "Adenosine instead of supranormal potassium in cardioplegia: It is safe, efficient, and reduces the incidence of postoperative atrial fibrillation. A randomized clinical trial", Journal of Thoracic and Cardiovascular Surgery, 2013, vol. 145(3), pp. 812-818.
Examination Report dated Mar. 14, 2018 in related Australian Patent Application No. 2015245903.
Extended European Search Report dated Mar. 9, 2018 in related EP Patent Application No. 15853016.2.
O'Blenes et al., "Protecting the aged heart during cardian surgery: The potential benefits of del Nido cardioplegia", Journal of Thoracic and Cardiovascular Surgery, 2011, vol. 141(3), pp. 762-770.
Takemoto, et al., "The reciprocal protective effects of magnesium and calcium in hyperkalemic cardioplegic solutions on ischemic myocardium", Basic Research in Cardiology, 1992, vol. 87(1), pp. 559-569.
Hearse, et al., "Protection of the myocardium during ischemic arrest. Dose response curves for procaine and lignocaine in cardioplegic solutions", Journal of Thoracic and Cardiovascular Surgery, 1981, vol. 81(6), pp. 873-879.
White, et al., "Impact of initial reperfusion temperature on the functional recovery of DCD hearts", Journal of Heart and Lung Transplantation, 2014, vol. 33(4 Supplement), p. S109.
White et al., "Impact of initial acidic reperfusion on the functional recovery of DCD hearts during ex vivo heart perfusion", Canadian Journal of Cardiology, 2014, vol. 30, pp. S252-252.
White et al., "Impact of initial acidic reperfusion on the functional recovery of DCD hearts during ex vivo heart perfusion"; Journal of Heart and Lung Transplantation, 2015, vol. 34(4 Supplement), pp. S269-270
Rudd, D.M. et al., "Eight Hours of Cold Statis Storage with Adenosine and Lidocaine (Adenocaine) Heart Preservation Solutions: Toward Therapeutic Suspended Animation" J. Thorac. Cardiovasc. Surg. vol. 142(6), pp. 1552-1561.

(Continued)

Primary Examiner — Ruth A Davis

(57) ABSTRACT

A solution comprises a preservation mixture comprising a calcium ion source; and a buffer for maintaining a pH of the solution. The molar concentration of calcium ion ($Ca^{2+}$) in the solution is from 0.18 to 0.26 mmol/L, and the pH is lower than 7.4 and higher than 6.6. A composition for preparing the solution may comprise adenosine, lidocaine, and a calcium source, wherein the molar ratio of adenosine:calcium is from 0.3:0.26 to 0.45:0.18, and the molar ratio of lidocaine:calcium is from 0.04:0.26 to 0.09:0.18. A donor heart may be reperfused with the solution. The solution may be used for reperfusion of a donor heart, such as at a temperature from about 25 to about 37° C. The donor may be a donor after circulatory death.

19 Claims, 31 Drawing Sheets

(56) References Cited

OTHER PUBLICATIONS

International Search Report dated Jul. 13, 2015 in PCT/CA2015/050297.
International Preliminary Report on Patentability dated Oct. 12, 2016 in PCT/CA2015/050297.
Taylor, et al., "Registry of the International Society for Heart and Lung Transplantation: Twenty-sixth Official Adult Heart Transplant Report—2009", J. Heart Lung Transplant, 2009, vol. 28(10), pp. 1007-1022.
Extended European Search Report dated Oct. 24, 2017 in related EP Patent Application No. 15775970.5.
G. Dobson et al., "Adenosine and lidocaine: a new concept in nondepolarizing surgical myocardial arrest, protection, and preservation", Journal of Thoracic and Cardiovascular Surgery, Mosby-Year Book, 2004, vol. 127(3), pp. 794-805.
C. White et al., "Impact of Reperfusion Calcium and pH on the resuscitation of hearts donated after circulatory death", The Annals of Thoracic Surgery, 2017, vol. 103(1), pp. 122-130.
Written Opinion dated Jul. 13, 2015 in PCT/CA2015/050297.
International Preliminary Report on Patentability dated Feb. 15, 2017 in PCT/CA2015/051084.
International Search Report dated Feb. 5, 2016 in PCT/CA2015/051084.
Written Opinion dated Feb. 5, 2016 in PCT/CA2015/051084.
Baker, "Calcium content of St. Thomas' II cardioplegic solution damages ischemic immature myocardium", The Annals of Thoracic Surgery, 1991, vol. 52(4), pp. 993-999.
Robinson et al., "Lowering the calcium concentration in St. Thomas' Hospital cardioplegic solution improves protection during hypothermic ischemia", J. Thorac. Cardiovasc. Surg., 1991, vol. 101(2), pp. 314-325.
Muhlbacher et al., "Preservation solutions for transplantation", Transplant Proc., 1999, vol. 31(5), pp. 2069-2070.
Non-final Office Action dated Jul. 25, 2018 in related U.S. Appl. No. 15/302,593.
Rudd, et al., "Toward a new cold and warm nondepolarizing, normokalemic arrest paradigm for orthotopic heart transplantation", The Journal of Thoracic and Cardiovascular Surgery, 2009, vol. 137(1), pp. 198-207.
Gao, et al., "Role of Troponin I Proteolysis in the Pathogenesis of Stunned Myocardium", Circulation Research, 1997, vol. 80(3), pp. 393-399.
Ebel, et al., "Lidocaine reduces ischaemic but not reperfusion injury in isolated rat heart", British Journal of Anaesthesia, 2001, vol. 86(6), pp. 846-852.
Ely, et al., "Protective effects of adenosine in myocardial ischemia", Circulation, 1992, vol. 85(3), pp. 893-904.
unitslab.com, Online Convertor, Lidocaine, retrieved Jul. 18, 2018.

\* cited by examiner

COMPOSITION AND SOLUTION WITH CONTROLLED CALCIUM ION LEVEL, AND RELATED METHOD AND USE FOR REPERFUSION

CROSS-REFERENCE TO RELATED APPLICATIONS

This application is a national filing of PCT International Patent Application No. PCT/CA2015/051084, filed Oct. 23, 2015, which is a continuation-in-part application of U.S. patent application Ser. No. 15/302,593, filed Oct. 7, 2016, which is a national filing of PCT International Patent Application No. PCT/CA2015/050297, filed Apr. 10, 2015, which claims the benefit of, and priority from, U.S. Provisional Patent Application No. 61/978,132, filed Apr. 10, 2014, the entire contents of each of which are incorporated herein by reference.

This application claims the benefit of, and priority from, U.S. Provisional Patent Application No. 62/068,524, filed Oct. 24, 2014, the entire contents of which are incorporated herein by reference.

FIELD

The present invention relates to novel compositions and solutions suitable for reperfusion and also relates to post-harvest preservation and protection of harvested donor hearts prior to their resuscitation and transplantation into recipient subjects.

BACKGROUND

Heart failure affects 10% of North Americans and is the leading hospital discharge diagnosis. The diagnosis of heart failure is accompanied by a survival outlook that is comparable to a major cancer. There are limited rehabilitation options available to patients who are suffering with heart failure, and few strategies actually rehabilitate the heart. Cardiac transplantation remains the gold-standard therapeutic intervention for patients with end-stage heart failure, with an increasing number of individuals being added to the transplant waiting list every year. However, wider application of this life-preserving intervention is limited by the availability of donors. Data from the International Society of Heart and Lung Transplantation Registry shows that cardiac transplantation is in progressive decline in suitable donors (2007, *Overall Heart and Adult Heart Transplantation Statistics*). Two hundred and fifty eight Canadians have died during the last decade (2000-2010; Heart and Stroke Foundation of Canada) while waiting for heart transplantation. Similarly, in the United States, 304 patients died in 2010 alone while waiting for heart transplantation (Organ Procurement and Transplantation Network, U.S. Dept. of Health & Human Services). This phenomenon is primarily due to a shortage of suitable organ donors, and it is being experienced across the globe.

Time is of the essence for removal of a heart from a donor and its successful transplantation into a recipient. The following conventional principles generally apply for optimal donor heart preservation for the period of time between removal from the donor and transplantation: (i) minimization of cell swelling and edema, (ii) prevention of intracellular acidosis, (iii) prevention of injury caused by oxygen free radicals, and (iv) provision of substrate for regeneration of high-energy phosphate compounds, particularly adenosine triphosphate (ATP), during reperfusion. There are two main sources of donor hearts for transplantation. First, breathing patients who have suffered irreversible loss of brain function as a result of blunt head trauma or intracerebral hemorrhage. Such a patient is referred to as a "brain-stem-dead" donor or a donor after brain death ("DBD"). Second, patients who have suffered circulatory death. Such a patient is referred to as a "non-heart-beating" donor, a "cardiac dead" donor, a donor after cardiac death, or a donor after circulatory death (DCD).

Brainstem-dead donors can be maintained under artificial respiration for extended periods of time to provide hemodynamic stability throughout their bodies until the point of organ retrieval. Cardiac perfusion is uncompromised and organ functionality is theoretically maintained. However, brainstem death itself can profoundly affect cardiac function. The humoral response to brainstem death is characterized by a marked rise in circulating catecholamines. Physiological responses to this "catecholamine storm" include vasoconstriction, hypertension and tachycardia, all of which increase myocardial oxygen demand. Increased levels of catecholamine circulating throughout the vascular system induce vasoconstriction, which, in turn, compromises myocardial oxygen supply and can lead to subendocardial ischemia. This imbalance between myocardial oxygen supply and demand is one factor implicated in the impairment of cardiac function following brainstem death (Halejcio-Delophont et al., 1998, *Increase in myocardial interstitial adenosine and net lactate production in brain-dead pigs: an in vivo microdialysis study*. Transplantation 66(10):1278-1284; Halejcio-Delophont et al., 1998, *Consequences of brain death on coronary blood flow and myocardial metabolism*. Transplant Proc. 30(6):2840-2841. Structural myocardial damage occurring after brainstem death is characterized by myocytolysis, contraction band necrosis, sub-endocardial hemorrhage, edema and interstitial mononuclear cell infiltration (Baroldi et al., 1997, *Type and extent of myocardial injury related to brain damage and its significance in heart transplantation: a morphometric study*. J. Heart Lung Transplant 16(10):9941000). In spite of no direct cardiac insult, brainstem-dead donors often exhibit reduced cardiac function, and the current understanding is that only 40% of hearts can be recovered from this donor population for transplantation.

Numerous perfusion apparatus, systems and methods have been developed for ex vivo maintenance and transportation of harvested organs. Most employ hypothermic conditions to reduce organ metabolism, lower organ energy requirements, delay the depletion of high energy phosphate reserves, delay the accumulation of lactic acid, and retard morphological and functional deteriorations associated with disruption of oxygenated blood supply. Harvested organs are generally perfused in these systems with solutions comprising antioxidants and pyruvate under low temperatures to maintain their physiological functionality.

The short-comings of hypothermic apparatus, systems and methods have been recognized by those skilled in these arts, and alternative apparatus, systems and methods have been developed for preservation and maintenance of harvested organs at temperatures in the range of about 25° C. to about 35° C. (this can be referred to as "normothermic" temperatures, though normothermic more conventionally means a normal body temperature, i.e., an average of about 37° C.). Normothermic systems typically use perfusates based on the Viaspan™ formulation (also known as the University of Wisconsin solution or UW solution) supplemented with one or more of the following: serum albumin as a source of protein and colloid; trace elements to potentiate viability and cellular function; pyruvate and adenosine for oxidative phosphorylation support; transferrin as an attachment factor; insulin and sugars for metabolic support; glutathione to scavenge toxic free radicals as well as a source of impermeant; cyclodextrin as a source of impermeant, scavenger, and potentiator of cell attachment and growth factors; a high $Mg^{2+}$ concentration for microvessel metabolism support; mucopolysaccharides for growth factor potentiation and hemostasis; and endothelial growth factors. For instance, Viaspan comprises potassium lactobionate, $KH_2PO_4$, $MgSO_4$, raffinose, adenosine, glutathione, allopurinol, and hydroxyethyl starch. Other normothermic perfusion solutions have been developed and used (Muhlbacher et al., 1999, *Preservation solutions for transplantation*. Transplant Proc. 31(5):2069-2070). While harvested kidneys and livers can be maintained beyond twelve hours in normothermic systems, normothermic bathing and maintenance of harvested hearts by perfusion beyond 12 hours results in deterioration and irreversible debilitation of the hearts' functionality. Another disadvantage of using normothermic, continuous-pulsed-perfusion systems for maintenance of harvested hearts is the time required to excise a heart from a donor, mount it into the normothermic perfusion system and then initiate and stabilize the perfusion process.

After the excised donor heart has been stabilized, its physiological functionality is determined and, if transplantation criteria are met, the excised heart is transported as quickly as possible to a transplant facility.

In the case of brainstem-dead donors, the heart generally is warm and beating when it is procured. It is then stopped, cooled, and put on ice until it is transplanted. Chilling the harvested heart reduces its metabolic activity and related demands by about 95%. However, some metabolic activity continues with the consequence that the heart muscle begins to die, and clinical data have shown that once the period of chilling of a harvested heart is prolonged beyond 4 hours, the risk of 1-year mortality post-transplant starts to rise. For example, risk of death at 1-year post-transplant for a recipient receiving a heart that has been preserved by chilling for six hours more than doubles compared to a recipient receiving a heart that has been chilled for less than 1 hour (Taylor et al., 2009, *Registry of the International Society for Heart and Lung Transplantation: Twenty-sixth Official Adult Heart Transplant Report—2009*. JHLT 28(10):1007-1022).

Well-defined criteria have been developed for harvesting organs for transplantation from non-heart-beating donors (Kootstra et al., 1995, *Categories of non-heart-beating donors*. Transplant Proc. 27(5):2893-2894; Bos, 2005, *Ethical and legal issues in non-heart-beating organ donation*. Transplantation, 2005. 79(9): p. 1143-1147). Non-heart-beating donors have minimal brain function but do not meet the criteria for brainstem death, and therefore such donors cannot be legally declared brainstem dead. When it is clear that there is no hope for meaningful recovery of the patient, the physicians and family must be in agreement to withdraw supportive measures. Up to this point in care, non-heart-beating patients are often supported with mechanical ventilation as well as intravenous inotropic or vasopressor medication. However, only those patients with single system organ failure, namely failure of the neurologic system, can be considered for organ donation. Withdrawal of life support, most commonly the cessation of mechanical ventilation, is followed by anoxic cardiac arrest, after which the patient must remain asystolic for five minutes before organ procurement is allowed. Consequently, the organs of non-heart-beating donors are necessarily exposed to variable periods of warm ischemia after cardiac arrest, which may result in varying degrees of organ damage. However, provided that the duration of warm ischemia is not excessive, many types of organs, such as kidneys, livers, and lungs, can be harvested from non-heart-beating donors and are able to recover function after transplantation with success rates that approximate those for transplanted organs from brainstem-dead donors. While hearts harvested from brain-dead donors are exposed to an ischemic period limited to the time from organ procurement to transplant, hearts harvested from donors after cardiac death are exposed to much greater ischemic insult events, including a hypoxemic arrest event, warm ischemic injury occurring during the mandatory five-minute stand-off period before organ harvesting may be commenced, and further ischemic injury occurring during reperfusion of the heart after it is harvested. Because of the ischemic damage that occurs before organ harvesting commences, hearts from non-heart-beating donors are not used for transplantation.

SUMMARY

The present disclosure includes a novel solution comprising a preservation mixture comprising a calcium ion source; and a buffer for maintaining a pH of the solution, wherein the molar concentration of calcium ion ($Ca^{2+}$) in the solution is from 0.18 to 0.26 mmol/L, and the pH is lower than 7.4 and higher than 6.6. The molar concentration of calcium ion ($Ca^{2+}$) may be 0.22 mmol/L. The pH may be from 6.8 to 7.0, such as 6.9. The preservation mixture may be a cardioplegia mixture comprising adenosine, lidocaine, and a magnesium ion source. The solution may comprise 0.3 to 0.45 mmol/L of adenosine, 0.04 to 0.09 mmol/L of lidocaine, and 11 to 15 mmol/L of $Mg^{2+}$. The solution may comprise a sodium ion source and a potassium ion source. The solution may comprise about 130 to about 160 mmol/L of $Na^+$ and 4 to 7 mmol/L of $K^+$. The solution may comprise chloride, an osmotic buffer and a reducing agent. The solution may comprise 70 to 140 or 70 to 180 mmol/L of chloride, 8 to 12.5 mmol/L of glucose, 7.5 to 12.5 IU/L of insulin, 100 to 140 mmol/L of D-mannitol, 0.75 to 1.25 mmol/L of pyruvate, and 2.5 to 3.5 mmol/L of reduced glutathione. The solution may comprise 0.3 to 0.45 mmol/L of adenosine; 0.04 to 0.09 mmol/L of lidocaine; 8 to 12.5 mmol/L of glucose; 110 to 130 mmol/L of NaCl; 4 to 7 mmol/L of KCl; 16 to 24 mmol/L of $NaHCO_3$; 0.9 to 1.4 mmol/L of $NaH_2PO_4$; 0.18 to 0.26 mmol/L of $CaCl_2$; 11 to 15 mmol/L of $MgCl_2$; 7.5 to 12.5 IU/L of insulin; 100 to 140 mmol/L of D-mannitol; 0.75 to 1.25 mmol/L of pyruvate; and 2.5 to 3.5 mmol/L of reduced glutathione. The solution may comprise 0.4 mmol/L of adenosine; 0.05 mmol/L of lidocaine; 10 mmol/L of glucose; 123.8 mmol/L of NaCl; 5.9 mmol/L of KCl; 20 mmol/L of $NaHCO_3$; 1.2 mmol/L of $NaH_2PO_4$; 0.22 mmol/L of $CaCl_2$; 13 mmol/L of $MgCl_2$; 10 IU/L of insulin; 120 mmol/L of D-mannitol; 1 mmol/L of pyruvate; and 3 mmol/L of reduced glutathione.

A composition for preparing the solution described in the preceding paragraph is also provided. The composition may comprise adenosine, lidocaine, and a calcium source, wherein the molar ratio of adenosine:calcium is from 0.3:0.26 to 0.45:0.18, and the molar ratio of lidocaine:calcium is from 0.04:0.26 to 0.09:0.18. The molar ratio of adenosine:calcium may be 0.4:0.22, and the molar ratio of lidocaine:calcium may be 0.05:0.22. The composition may further comprise a sodium source, a potassium source and a magnesium source, wherein the molar ratio of calcium:sodium is from 0.26:130 to 0.18:160, the molar ratio of calcium:

potassium is from 0.26:4 to 0.18 to 7, and the molar ratio of calcium:magnesium is from 0.26:11 to 0.18:15. The molar ratio of calcium:sodium may be 0.22:147, the molar ratio of calcium:potassium may be 0.22:5.9, and the molar ratio of calcium:magnesium may be 0.22:13. The composition may also comprise chloride, glucose, insulin, D-mannitol, pyruvate, and reduced glutathione.

The solution as described herein may be used to reperfuse a donor heart and the present disclosure includes a method of reperfusion of a donor heart and use of the solution described herein for reperfusion of a donor heart. The heart may be reperfused with the solution during removal of the heart from the donor. The heart after removal from the donor may be reperfused in a reperfusion device. The heart may be reperfused with the solution for at least 3 minutes immediately after removal of the heart from the donor. The donor may be a donor after circulatory death. The reperfusion may be at a temperature above about 25° C. and below about 37° C. The reperfusion may be at a temperature of about 35° C. during reperfusion.

In such method or use, selected embodiments of the present disclosure relate to solutions for immersion and bathing of a harvested heart while being concurrently flowed through the heart and its vasculature.

Some embodiments of the present disclosure pertain to use of solutions for ex vivo maintenance of harvested hearts to reduce and ameliorate post-harvest ischemic damage.

Some embodiments of the present disclosure pertain to methods for ex vivo maintenance of harvested hearts to minimize the occurrence and extent of post-harvest ischemic damage.

BRIEF DESCRIPTION OF THE DRAWINGS

In the figures, which illustrate, by way of examples only, embodiments of this invention:

FIG. 7(A) is a representative micrograph of a section through a harvested pig heart reperfused at 5° C. showing swollen endothelial cells lining a capillary, while FIG. 7(B) is a representative micrograph of a section through a harvested pig heart reperfused at 35° C. showing normal endothelial cells lining a capillary;

DETAILED DESCRIPTION

Figure 1:
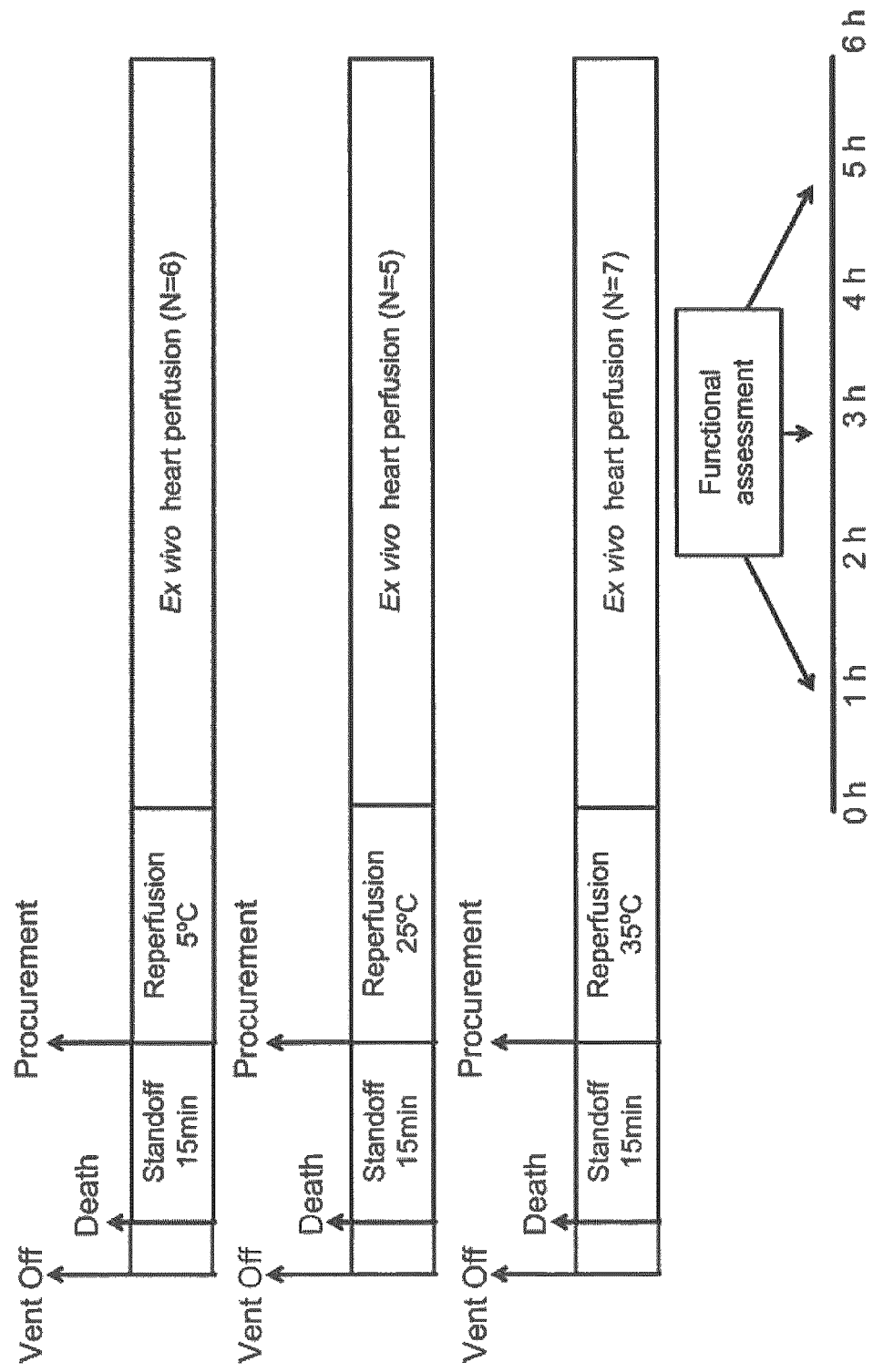
FIG. 1 ("FIG. 1) is a schematic flowchart outlining the experimental protocols used in Example 1.

Unless otherwise defined, all technical and scientific terms used herein have the same meaning as commonly understood by one of ordinary skill in the art to which this invention belongs. In order that the invention herein described may be fully understood, the following terms and definitions are provided herein.

The word "comprise" or variations such as "comprises" or "comprising" will be understood to imply the inclusion of a stated integer or groups of integers but not the exclusion of any other integer or group of integers.

The term "about" or "approximately" means within 20%, preferably within 10%, and more preferably within 5% of a given value or range.

The term "afterload" means the mean tension produced by a chamber of the heart in order to contract. It can also be considered as the 'load' that the heart must eject blood against. Afterload is therefore a consequence of aortic large vessel compliance, wave reflection and small vessel resistance (left ventricular afterload) or similar pulmonary artery parameters (right ventricular afterload).

The term "preload" refers to the stretching of a single cardiac myocyte immediately prior to contraction and is therefore related to the sarcomere length. Since sarcomere length cannot be determined in the intact heart, other indices of preload such as ventricular end diastolic volume or pressure are used. As an example, preload increases when venous return is increased.

The term "cardiac myocyte" means a cardiac muscle cell.

The term "stroke volume" (SV) means the volume of blood ejected by the right/left ventricle in a single contraction. It is the difference between the end diastolic volume (EDV) and the end systolic volume (ESV). Mathematically, SV=EDV−ESV. The stroke volume is affected by changes in preload, afterload and inotropy (contractility). In normal hearts, the SV is not strongly influenced by afterload whereas in failing hearts, the SV is highly sensitive to afterload changes.

The term "stroke work" (SW) refers to the work performed by the left or right ventricle to eject the stroke volume into the aorta or pulmonary artery, respectively. The area enclosed by the pressure/volume loop is a measure of the ventricular stroke work, which is a product of the stroke volume and the mean aortic or pulmonary artery pressure (afterload), depending on whether one is considering the left or the right ventricle.

The term "ejection fraction" (EF) means the fraction of end diastolic volume that is ejected out of the ventricle during each contraction. Mathematically, EF=SV/EDV. Healthy ventricles typically have ejection fractions greater than 0.55. Low EF usually indicates systolic dysfunction and severe heart failure can result in EF lower than 0.2. EF is also used as a clinical indicator of the inotropy (contractility) of the heart. Increasing inotropy leads to an increase in EF, while decreasing inotropy decreases EF.

The term "end systolic pressure volume relationship" (ESPVR) describes the maximal pressure that can be developed by the left ventricle at any given left ventricular volume, or alternatively, by the right ventricle at any given right ventricular volume. This implies that the PV loop cannot cross over the line defining ESPVR for any given contractile state. The slope of ESPVR (Ees) represents the end-systolic elastance, which provides an index of myocardial contractility. The ESPVR is relatively insensitive to changes in preload, afterload and heart rate. This makes it an improved index of systolic function over other hemodynamic parameters like ejection fraction, cardiac output and stroke volume. The ESPVR becomes steeper and shifts to the left as inotropy (contractility) increases. The ESPVR becomes flatter and shifts to the right as inotropy decreases.

The term "preload recruitable stroke work relationship" (PRSW) means a measure of cardiac contractility, and is the linear relationship between SW and EDV.

The term "pressure-volume area" (PVA) means the total mechanical energy generated by ventricular contraction. This is equal to the sum of the stroke work (SW), encompassed within the PV loop, and the elastic potential energy (PE). Mathematically, PVA=PE+SW.

The term "dP/dt max" is a measure of the global contractility of the left ventricle. The greater the contractile force exerted during systole, the greater the rate of increase in left ventricular pressure.

The term "dP/dt min" is a measure of the relaxation of the left ventricle during diastole.

As used herein, the term "DCD" means donor after circulatory death, or donor after cardiac death. As used herein, the term "DBD" means donor after brain death.

The term "Langendorff perfusion" refers to a method of perfusing an excised heart with a nutrient-rich oxygenated solution in a reverse fashion via the aorta. The backwards pressure causes the aortic valve to shut, thereby forcing the solution into the coronary vessels that supply the heart tissue with blood. This transports nutrients and oxygen to the cardiac muscle, allowing it to continue beating for several hours after its removal from the animal.

The term "working heart" as used herein, refers to clinical ex vivo coronary perfusion throughout an excised heart by ventricular filling via the left atrium and ejection from the left ventricle via the aorta driven by the heart's contractile function and regular cardiac rhythm. The excised heart is attached by cannulae to a perfusate reservoir and circulatory pumps in a Langendorff preparation. The flow of perfusate through the excised heart in "working heart" mode is in the direction opposite to the flow of perfusate during Langendorff perfusion.

The term "ischemia" means a condition that occurs when blood flow and oxygen are kept from the heart.

The term "reperfusion" as used herein means passing a solution through a heart to re-establish supply of oxygen and provide protective or preservation materials to the heart, such as by pumping the solution through the heart in a perfusion device, and optionally immersing the heart in the solution. Optionally, during reperfusion the heart may be immersed in an oxygen-rich perfusate solution, which may be the same as the reperfusion solution or may be a different solution.

The term "reperfusion injury" as used herein refers to tissue damage in a harvested heart that occurs when a supply of oxygen via a perfusate solution is provided to the tissue after a period of ischemia or lack of oxygen. Depriving the heart of sufficient oxygen and nutrients during the ischemic period creates a condition in which the restoration of circulation results in inflammation and oxidative damage through the induction of oxidative stress, rather than restoration of normal function.

The term "cardioplegia" as used herein means an intentional and temporary cessation of, or maintenance of ceased or reduced, cardiac activities, such as by arresting or stopping the beating of the heart, for the purpose of preserving the health of the myocardium, including through a period of significantly reduced provision of oxygen and metabolic substrate. Cardioplegia can be imposed on a beating heart by chilling or by administration of a solution containing one or more chemicals that will cause paralysis of the heart muscle, or by both concurrently. In embodiments of the present disclosure, cardioplegia may also be achieved by providing limited oxygen and other supplies to the myocardium to preserve its health without fully restoring the cardiac activities of the heart.

The term "cardioplegic solution" as used herein means a solution containing chemical components that cause or maintain asystole (paralysis) of the heart in a mixture with components to preserve or protect heart cell functions.

The term "homeostasis" as used herein means the maintenance of a fairly stable metabolic equilibrium within and between the muscle cells of a harvested heart.

The term "normokalemic" as used herein means having or characterized by a normal concentration of potassium ion in the blood. Normal serum potassium ion levels in human blood are in a range between 3.5 mEq/L and 5.0 mEq/L.

The term "hyperkalemic" as used herein means having or characterized by a concentration of potassium ion in the blood that is significantly elevated over a normokalemic concentration. A hyperkalemic concentration includes any potassium ion concentration in excess of 6.0 mEq/L.

The term "hypothermic" as used herein means a temperature that is less than about 20° C.

The medically and legally prescribed events that must occur for ethical procurement of transplantable hearts from donors after circulatory death (DCD) inevitably cause an occurrence of cardiac arrest and a sequence of ischemic events resulting in damage to the heart muscles. These prescribed events cannot be modified.

Ischemia is accompanied by significant changes in ion-exchange patterns into and out of heart muscle cells as a consequence, primarily, of the loss of oxygen supply. As the availability of oxygen decreases and stops, the metabolism of the heart muscle cells shifts from aerobic to anaerobic with an immediate consequence of rapidly decreasing intracellular pH levels. Low intracellular pH results in increasing amounts of $H^+$ ions being excreted from the muscle cells into the extracellular spaces. At the same time, the ion potential across the cellular membranes diminishes due to significantly reduced $Na^+/Ca^{2+}$ ion exchange as a result of lower intracellular ATP levels. The ultimate result is an increasing overload in intracellular $Ca^{2+}$ levels. The increased levels of intracellular $Ca^{2+}$ activate $Ca^{2+}$-dependent proteases, which disrupt cell structure resulting in cell death. The severity of such damage increases with the duration of the ischemic conditions.

Ischemic damage occurring during the procurement of a donor heart may be reduced by reperfusion of the harvested heart as soon as possible after its harvest in blood or a blood replacement product, as exemplified by Viaspan and CELSIOR® (CELSIOR is a registered trademark of Genzyme Corp., Cambridge, Mass., U.S.A.). Reperfusion causes a prompt increase in the extracellular pH, which results in robust excretion of $H^+$ ions into the extracellular space. $H^+$ ion movement into the extracellular space drives $Na^+$ ions into the cells. Higher intracellular $Na^+$ ion concentrations reverse the $Na^+/Ca^{2+}$ ion exchanger across the myocyte cell membranes, resulting in "reverse mode" excretion of accumulated intracellular $Na^+$ ions accompanied by an influx of $Ca^{2+}$ ions, recovery of ATP synthesis, and a subsequent re-excretion of $Ca^{2+}$ ions. However, although reperfusion may re-establish aerobic respiration and metabolism in harvested hearts, reperfusion commonly results in further damage (known as reperfusion injury) to the heart muscle cells. For example, the immediate increase in intracellular pH levels results in the generation of reactive oxygen species that activate subcellular signals that in turn activate inflammatory cascades leading to apoptosis and cytokine release. Additionally, reactive oxygen species directly disrupt DNA structures and protein structures, thereby causing cell death. Another problem associated with conventional reperfusion techniques is that it is very difficult in these techniques to modulate the intracellular levels of $Ca^{2+}$ ions during the reperfusion process, where reperfusion further increases the intracellular overload of $Ca^{2+}$ ions in heart muscle cells.

Contraction of a heart while the heart muscle cells are overloaded with intracellular $Ca^{2+}$ ions during reperfusion inevitably results in a disruptive type of necrosis, termed contraction band necrosis, as a result of massive myofibril contraction. Contraction band necrosis is considered to be the most severe form of reperfusion injury.

Accordingly, the rationale for chilling donor hearts immediately after their procurement and during reperfusion is to reduce metabolic activity within the heart muscle cells as quickly as possible to minimize the generation of reactive oxygen species during reperfusion and to minimize a subsequent intracellular overload of $Ca^{2+}$ ions during reperfusion.

We have discovered that myocardial injury to donor hearts may be minimized by a strategy focused on maintaining calcium ion homeostasis in and about the heart during the harvesting and the reperfusion processes. Our strategy comprises two components wherein the first component is an oxygenated cardioplegic composition for use as reperfusate solution during procurement of a harvested heart and for a period of time immediately after harvest during which the harvested heart is reperfused, preferably, for at least 3 minutes. The reperfusate solution causes an immediate cessation of a donor heart's rhythmic beating upon reperfusion. The at-least-3-minute reperfusion period, starting immediately after the heart is harvested, is referred to as the immediate-early ("IE") period. The second component of our strategy is to avoid chilling the heart during procurement process and during the post-harvest reperfusion period, and instead maintain normothermic conditions during harvest, during IE reperfusion, and during subsequent ex vivo maintenance of the harvested heart.

It has been recognized that it would be beneficial to prevent myocyte contraction before intracellular calcium overload in a donor heart has been resolved, and before ATP stores in the heart can be repleted. It is expected that after a period of reperfusion or perfusion, as oxygen and energy substrates are delivered to the heart, the heart can start beating again. However, if the heart starts beating again when there is intracellular calcium overload, it can result in contracture. Thus, it is expected that reducing intracellular calcium ion concentration to eliminate or prevent intracellular calcium overload before restarting myocyte contraction, or fully restoring cardiac activities, can reduce reperfusion injuries. Our results indicate that intracellular calcium concentrations and consequently reperfusion injuries may be reduced by controlling, at least in part, the calcium contents in the reperfusion solution.

When selecting components and their concentrations in a cardioplegic composition for reperfusion, for example of a DCD heart for transplant, at temperatures from about 25 to about 37° C., a number of factors may need to be considered. To reduce or minimize myocardial injury to such a donor heart during reperfusion, a balanced approach in view of these factors may be required. For example, a source of potential complication is that the intracellular concentrations of a particular ion, especially the intracellular concentration of $Ca^{2+}$ or $H^+$ ions, which if not properly controlled could contribute to myocardial injury, can be sensitive to the extracellular concentrations of these ions as well as other ions. For instance, the intracellular concentration of $Ca^{2+}$ in myocytes is expected to be affected not only by the extracellular concentration of $Ca^{2+}$, but also, as a result of particular ion exchanges in the plasma membrane, by extracellular concentrations of other ions, such as $H^+$ and $Na^+$. Thus, the intracellular calcium ion concentration may be adjusted by changing extracellular concentration of one or more of $Ca^{2+}$, $Na^+$ and $H^+$. However, changing the extracellular concentrations of $H^+$ and $Na^+$ may result in other changes which can affect other aspects of myocardial injury, in addition to optimizing intracellular $Ca^{2+}$. Another factor to be considered is provision of sufficient calcium ions in the reperfusion solution to avoid a phenomenon known as "calcium paradox"—where hypocalcemic cardiac muscles are re-exposed to normal level of $Ca^{2+}$, the cells can become overloaded with $Ca^{2+}$, which can cause significant cell injuries or damages. To achieve the optimal results, these different effects should be considered in a balanced approach when selecting the components and their respective concentrations.

In an embodiment, a solution for use as a reperfusion solution may include the following components:

A preservation mixture which may include adenosine to provide oxidative phosphorylation support, and lidocaine to prevent myocyte contraction during reperfusion. Additionally, a relatively high concentration of $Mg^{2+}$ may also be included, as hypermagnesemia is also expected to assist in prevention of myocyte contraction during reperfusion. For example, the mixture may contain 0.3 to 0.45 mmol/L of adenosine, 0.04 to 0.09 mmol/L of lidocaine and 11 to 15 mmol/L of $Mg^{2+}$.

$Ca^{2+}$ at a concentration of 0.18 mmol/L to 0.26 mmol/L, to provide for a lower than the physiological concentration of extracellular calcium ions in a normal heart.

$Na^+$, such as at a concentration of 130 mmol/L to 160 mmol/L, to provide for an appropriate concentration of extracellular sodium ion.

$K^+$ in a normakalemic concentration, such as, 4 to 7 mmol/L.

$Cl^-$ in a concentration ranging, for example, from 70 to 180 mmol/L. While in some embodiments, the $Cl^-$ concentration may be higher, such as up to about 180 mmol/L in the solution, it may be beneficial in some embodiments to have a lower $Cl^-$ concentration such as for example, from 70 to 140 mmol/L, or up to about 140 mmol/L.

A pH-buffer for maintaining the pH of the reperfusion solution to be higher than 6.7 and less than 7.4 at the desired operation temperature for reperfusion. The pH-buffer may be provided by, for example, a combination of 16 to 24 mmol/L of $HCO_3^{1-}$ and 0.9 to 1.4 mmol/L of $H_2PO_4^{1-}$.

Substrates for energy metabolism, such as a combination of 8 to 12.5 mmol/L of glucose and 0.75 to 1.25 mmol/L of pyruvate.

An osmotic agent in a concentration for obtaining an appropriate osmolarity, such as, 100 to 140 mmol/L of D-mannitol.

An antioxidant or reducing agent in a concentration for obtaining an appropriate degree of protection from reactive oxygen species and physiological levels of reduction, such as, 2.5 to 3.5 mmol/L of reduced glutathione.

Optionally, one or more growth factors, such as, 7.5 to 12.5 IU/L of insulin.

During use, a pre-prepared cardioplegic composition may be titrated to the desired pH prior to use, such that the composition at the desired temperature for reperfusion is at the desired pH at the moment of reperfusion.

A cardioplegic composition for causing an immediate cessation of a donor heart's rhythmic beating upon its contact with the cardioplegic composition may comprise an adenosine-lidocaine mixture, a normokalemic concentration of potassium ions, a concentration of $Ca^{2+}$ ions selected to maintain the intracellular level of $Ca^{2+}$ ions in the harvested heart's muscle cells at about $10^{-4}$ mmol/L, and a pH of 6.9. A suitable adenosine-lidocaine mixture may comprise 300 μmol/L, 325 μmol/L, 350 μmol/L, 375 μmol/L, 400 μmol/L, 425 μmol/L, 450 μmol/L of adenosine and 40 μmol/L, 45 μmol/L, 50 μmol/L, 55 μmol/L, 60 μmol/L, 70 μmol/L, 80 μmol/L, 90 μmol/L of lidocaine. The cardioplegic composition may additionally comprise 8.012.5 mmol/L of glucose, 120-140 mmol/L of NaCl, 4.0-7.0 mmol/L of KCL, 12.0-16.0 mmol/L of $NaHCO_3$, 0.9-1.4 mmol/L of $NaH_2PO_4$, 0.18-0.26 mmol/L of $CaCl_2$, 11.0-15.0 mmol/L of $MgCl_2$, 7.5-12.5 IU/L of insulin, 100.0-140.0 mmol/L of D-mannitol, 0.75-1.25 mmol/L of pyruvate, and 2.5-3.5 mmol/L of reduced glutathione. In a particular embodiment, a cardioplegic composition may include 400 μmol/L of adenosine, 50 μmol/L of lidocaine, 10.0 mmol/L of glucose, 123.8 mmol/L of NaCl, 5.9 mmol/L of KCl, 20 mmol/L of $NaHCO_3$, 1.2 mmol/L of $NaH_2PO_4$, 0.22 mmol/L of $CaCl_2$, 13.0 mmol/L of $MgCl_2$, 10.0 IU/L of insulin, 120.0 mmol/L of D-mannitol, 1.0 mmol/L of pyruvate, and 3.0 mmol/L of reduced glutathione.

The cardioplegic composition may be oxygenated by bubbling a stream of O2 gas through the cardioplegic composition prior to and during its use for bathing and reperfusing a harvested donor.

Another selected embodiment of the present disclosure pertains to use of the selected oxygenated cardioplegic composition to reperfuse a harvested heart at a temperature of about 35° C. Accordingly, the selected oxygenated cardioplegic composition is warmed to about 35° C. before contacting the heart during procurement and subsequent IE reperfusion for at least 3 minutes after procurement has been completed. After the initial IE reperfusion period in the selected oxygenated cardioplegic composition under normothermic conditions, the harvested heart may be resuscitated by installation into a suitable apparatus for ex vivo maintenance of a functioning systolic harvested heart, by interconnection of conduit infrastructures provided within the apparatus with the heart's aorta, pulmonary artery, pulmonary vein, and vena cava, and bathing the excised heart in a constantly flowing perfusate solution comprising oxygenated blood and/or an oxygenated blood replacement solution. Additionally the constantly flowing perfusion solution is flowed through the heart's chambers while it is maintained in the apparatus. Such apparatus are generally configured with the following: (i) a perfusate pumping system; (ii) flow sensors for monitoring the flow of perfusate to and from the installed heart's aorta, pulmonary artery, pulmonary vein, and vena cava; (iii) an ECG apparatus interconnectable with the excised heart; (v) probes interconnecting the installed heart with instruments for monitoring the excised heart's physiological functionality using load independent indices and load dependent indices; and optionally (vi) pacemakers for initiating or maintaining systolic function of the heart.

It is expected that use of an example oxygenated cardioplegic composition disclosed herein to reperfuse a heart removed from a donor for transplant may provide a harvested heart with the ionic complement necessary for the ex vivo-maintained heart to continue generating ATP and pumping excess calcium out of the heart muscles cells while keeping the heart in a paralyzed condition i.e., a non-beating asystolic condition, thereby minimizing the potential for occurrence of contraction band necrosis. While not wishing to be bound by any particular theory, it is likely that use of such a cardioplegic composition for reperfusion of harvested hearts at temperatures from about 25 to about 35° C. can facilitate rapid restoration of calcium ion homeostasis and facilitate more rapid recovery and functional operation of the harvested heart after transplantation into a recipient subject.

Without being limited to any particular theory, it is also expected that when a heart removed from a DCD donor is reperfused immediately after its removal from the donor with a suitable cardioplegic solution with controlled calcium ion concentration and pH for a sufficient time, it is possible to avoid excessive reperfusion injuries, such as those caused by intracellular calcium overload, in the heart, without chilling the DCD heart to below about 25° C. before, during and after reperfusion, and to provide a heart suitable for transplantation.

In an embodiment, such a solution may include a cardioplegia mixture. The mixture contains a calcium ion source and a buffer for maintaining a pH of the solution. The molar concentration of calcium ion ($Ca^{2+}$) in the solution is from 0.18 to 0.26 mmol/L and the pH is lower than 7.4 and higher than 6.6. The molar concentration of calcium ion ($Ca^{2+}$) in the solution may be 0.22 mmol/L. The pH may be from 6.8 to 7.0, such as 6.9. In specific embodiments, the cardioplegia mixture may include adenosine, lidocaine, and a magnesium ion source, such as 0.3 to 0.45 mmol/L of adenosine, 0.04 to 0.09 mmol/L of lidocaine, and 11 to 15 mmol/L of $Mg^{2+}$. The solution may also include a sodium ion source and a potassium ion source, such as about 130 to about 160 mmol/L of $Na^+$ and 4 to 7 mmol/L of $K^+$. The solution may further include chloride, an osmotic buffer and an antioxidant or reducing agent. For example, suitable osmotic buffers may include D-manitol, lactobionate, dextran, albumin, or the like. Suitable antioxidants may include reduced glutathione, resveratrol, apelin analogs or the like. The solution may contain, for example, 70 to 140 mmol/L chloride, 100 to 140 mmol/L of D-mannitol, and 2.5 to 3.5 mmol/L of reduced glutathione. The solution may contain substrates for energy metabolism, such as one or more of glucose, pyruvate, free fatty acids (e.g. oleate or palmitate), triglycerides, or the like. For instance, in some embodiments, the solution may contain 8 to 12.5 mmol/L of glucose and 0.75 to 1.25 mmol/L of pyruvate. The solution may contain one or more growth factors, such as insulin, cardiotrophin-1, erythropoietin, platelet-derived growth factors (PDGF), various forms of fibroblast growth factors (FGF), or the like. For example, the solution may contain 7.5 to 12.5 IU/L of insulin. Thus, depending on the application, the solution may contain 0.3 to 0.45 mmol/L of adenosine; 0.04 to 0.09 mmol/L of lidocaine; 8 to 12.5 mmol/L of glucose; 110 to 130 mmol/L of NaCl; 4 to 7 mmol/L of KCl; 16 to 24 mmol/L of $NaHCO_3$; 0.9 to 1.4 mmol/L of $NaH_2PO_4$; 0.18 to 0.26 mmol/L of $CaCl_2$; 11 to 15 mmol/L of $MgCl_2$; 7.5 to 12.5 IU/L of insulin; 100 to 140 mmol/L of D-mannitol; 0.75 to 1.25 mmol/L of pyruvate; and 2.5 to 3.5 mmol/L of reduced glutathione. More specifically, the solution may contain 0.4 mmol/L of adenosine; 0.05 mmol/L of lidocaine; 10 mmol/L of glucose; 123.8 mmol/L of NaCl; 5.9 mmol/L of KCl; 20 mmol/L of $NaHCO_3$; 1.2 mmol/L of $NaH_2PO_4$; 0.22 mmol/L of $CaCl_2$; 13 mmol/L of $MgCl_2$; 10 IU/L of insulin; 120 mmol/L of D-mannitol; 1 mmol/L of pyruvate; and 3 mmol/L of reduced glutathione.

In different embodiments, a solution for reperfusion of an excised heart may include a cardioplegia mixture containing an anesthetic agent for paralyzing the heart and preventing myocyte contraction during reperfusion; and agents for protecting or restoring cardiac functions of the heart, the agents comprising a calcium source, a sodium source, and a potassium source, in amounts selected to restore and maintain calcium ion homeostasis in the heart at a temperature from about 25 to about 35° C. The solution may be at a temperature from about 25 to about 35° C., such as about 35° C.

As can be appreciated by those skilled in the art, a solution disclosed herein may be prepared and stored before use, or the solution may be prepared just before use by mixing pre-packaged compositions or materials, or by adding a solvent such as water or a buffer solution to a pre-formulation to form the desired solution. For example, a composition for preparing a reperfusion solution may include a mixture of adenosine, lidocaine, and a calcium source. The molar ratio of adenosine:calcium may be from 0.3:0.26 to 0.45:0.18, such as 0.4:0.22, and the molar ratio of lidocaine:calcium may be from 0.04:0.26 to 0.09:0.18, such as 0.05:0.22. The composition may also contain a sodium source, a potassium source and a magnesium source. The molar ratio of calcium:sodium may be from 0.26:130 to 0.18:160, such as 0.22:147. The molar ratio of calcium:potassium may be from 0.26:4 to 0.18 to 7, such as 0.22:5.9. The molar ratio of calcium:magnesium may be from 0.26:11 to 0.18:15, such as 0.22:13. The composition may also contain chloride, and one or more of glucose, insulin, D-mannitol, pyruvate, and reduced glutathione. The composition may be mixed with a suitable pH buffer to prepare the desired reperfusion solution, such as a selected reperfusion solution described herein.

Further embodiments relate to methods of preserving and preparing hearts for transplantation. For example, in a method for reperfusion of a heart for transplant, the heart may be reperfused with a reperfusion solution disclosed herein in a reperfusion device. The reperfusion device may be similar to a conventional perfusion device and may be operated similarly except replacing the perfusion solution with a reperfusion solution described herein. For example, the Quest MPS®2 Myocardial Protection System, provided by Quest Medical Inc., Allen, Tex., USA, may be used as the reperfusion device. A volume infusion pump may also be used to pump the reperfusion solution. An infuser, such as one that is typically used by a trauma patient, or a similar infuser, may be used for reperfusion. For example, Belmont™ rapid infuser RI-2 may be used in the reperfusion device.

The heart may be reperfused with the reperfusion solution for at least 3 minutes immediately after removal of the heart from the donor of the heart. The donor may be a DCD donor, and the DCD heart may be maintained at a temperature above about 25° C. and below about 37° C., such as at about 35° C. at any stage of the procurement, reperfusion, perfusion, storage, and transplantation procedures.

Further embodiments are related to methods of maintaining a heart for transplant. For example, the heart may be treated to maintain calcium ion homeostasis in the heart at a temperature from about 25° C. to about 37° C., such as by use of a suitable solution or composition disclosed herein.

As now can be appreciated, embodiments of solutions disclosed herein may be used for reperfusion of a donor heart, during removal of the heart, or immediately after removal of the heart from the donor, or both. Further, the solution may also be used as perfusion solution at other times or for other purposes as may be appropriate. Conveniently, the heart may be removed from a donor after circulatory death (DCD) at a temperature from about 25 to 37° C. In different embodiments, a solution as described herein may also be used for reperfusion of other types of hearts such as a heart removed from a donor after brain death (DBD). In some embodiments, the solution may also be used at lower temperatures.

While some embodiments have been described herein with reference to reperfusion or cardioplegic solutions or compositions, or cardioplegia mixtures, it can be understood that they are preservation compositions, solutions or mixtures, which can preserve or protect cell functions and therefore the health of the cell in the organ to be transplanted.

The following examples are provided to more fully describe the disclosure and are presented for non-limiting, illustrative purposes.

EXAMPLES

The sample cardioplegic solutions used in these Examples were prepared at room temperature and their stated pH was measured at room temperature. The lidocaine and D-mannitol solutions used to prepare the sample solutions were obtained from commercial sources.

All sample solutions were prepared by adding the component ingredients to water. The water was double-deionized and sterilized as known to those skilled in the art. The sample solutions were oxygenated before use.

Example 1

It is apparent that strategies to minimize post-harvest ex vivo trauma and injury to donor hearts require an understanding of ionic changes that occur in the heart during ischemia and during/after reperfusion.

During ischemia, the heart's metabolism shifts from aerobic to anaerobic with a subsequent production of protons within the cardiac myocytes. The excess protons efflux through the myocyte cell walls in exchange for ingressing $Na^+$ ions through $Na^+/K^+$ pump. As the ATP reserves within the myocytes are depleted, the myocytes become unable to pump the ingressing $Na^+$ ions back out through the $Na^+/K^+$ pump. As a result, as the duration of ischemia progresses, there is an accumulation of: (i) $Na^+$ ions within the myocytes, and (ii) $Na^+$ ions and $H^+$ ions inside and outside the myocytes.

During reperfusion, the $H^+$ ions on the outside of the myocytes are washed away resulting in the occurrence of a large $Na+/H^+$ gradient across the myocyte walls resulting in a large influx of $Na^+$ ions into the myocytes. The increased concentration of $Na^+$ ions causes the $Na^+/Ca^{2+}$ pump to work in a reverse mode resulting in an influx of $Ca^{2+}$ ions into the myocytes as the $Na^+/Ca^{2+}$ pump attempts to equilibrate the levels of $Na^+$ ions inside and outside of the myocytes. If a $Ca^{2+}$-overloaded myocyte is allowed to contract, a fatal hypercontracture may occur (the hypercontracture is also commonly referred to as "contraction band necrosis"). Consequently, a primary goal of resuscitating a DCD heart is to mitigate a $Ca^{2+}$ ion overload in the myocytes.

Accordingly, our goals were to prevent a harvested DCD heart from contracting by reperfusion with an anesthetic-containing cardioplegic solution while providing the requisite substrates for regenerating ATP so that the reperfused heart could restore its homeostasis by pumping $Na^+$ ions and $Ca^{2+}$ ions and thereby minimize ischemia reperfusion trauma and injury. Because the generation of ATP to provide the energy necessary to exchange ions across the $Na^+/K^+$ pumps and the $Na^+/Ca^{2+}$ pumps, it was our idea that reperfusion of harvested donor hearts would facilitate more rapid restoration of ion homeostasis and recovery of cardiac function. Accordingly, the first study assessed the effects of reperfusion temperature on harvested donor hearts.

Eighteen pigs were separated into three groups and then euthanized following standard protocols and medical ethics procedures following the schematic flowchart shown in FIG. 1.

Six pigs were assigned to the first group ("chilled" group). Immediately after procurement of each heart was completed, each heart was installed into a Quest MPS®2 Myocardial Protection System (MPS is a registered trademark of Quest Medical Inc., Allen, Tex., USA) for precise control of the reperfusion pressure and temperature. The harvested hearts from first group of pigs were perfused for 3 minutes with a sample oxygenated cardioplegic composition (see TABLE I) that was chilled to 5° C. prior to commencing the reperfusion process. The cardioplegic composition was initially prepared at room temperature and the pH of the composition was measured at room temperature. The aortic perfusion pressure, coronary artery flow, and myocardial temperature were constantly monitored and recorded by the MPS®2 apparatus during the 3-minute initial reperfusion period. Blood gas samples were measured at 0, 30, 60, 120, and 180 seconds of the initial reperfusion period to collect data pertaining to changes occurring the partial pressure of $O_2$ ($PaO_2$), partial pressure of $CO_2$ ($PaCO_2$), pH levels, electrolyte levels, lactate levels among others.

TABLE I

| Sample I—Cardioplegic solution (pH = 7.35) | | |
|---|---|---|
| Constituent | mmol/L | IU/L |
| Adenosine | 0.4 | |
| Lidocaine | 0.5 | |
| Glucose | 10 | |
| NaCl | 111.8 | |
| KCl | 5.9 | |
| NaHCO$_3$ | 32 | |
| NaH$_2$PO$_4$ | 1.2 | |
| CaCl$_2$ | 0.22 | |
| MgCl$_2$ | 2.6 | |
| D-Mannitol | 120 | |
| Pyruvate | 1 | |
| Reduced glutathione | 3 | |
| Insulin | | 10 |

After the initial 3-minute reperfusion period was completed. Each heart was removed from the Quest MPS®2 apparatus and transferred into an ex vivo heart perfusion (EVHP) apparatus where it was perfused with a constantly flowing supply of a blood-STEEN solution mixture (Hb 45 g/L; XVIVO Perfusion Inc., Englewood, Colo., USA) wherein its systolic function was restored and maintained in a Langendorff mode at a normothermic temperature of 35° C. for 6 hours. The aortic pressure and heart rate were constantly monitored and processed using the LABCHART® software (LABCHART is a registered trademark of ADInstruments Pty. Ltd., Bella Vista, NSW, Australia). After 1 hour, 3 hours, and 5 hours of perfusion with the blood-STEEN solution mixture in the EVHP apparatus, each heart was transitioned from the Langendorff mode to a working mode by bringing the left atrial pressure from 0 to 8 mmHg and pacing the heart at 100 beats per minutes ("bpm"). Cardiac output, coronary blood flow, aortic root, and coronary sinus blood gases were measured, and cardiac function was assessed with a pressure-volume loop catheter. After these measurements were completed, each heart was immediately returned to the Langendorff mode.

Five pigs were assigned to the second group ("cooled" group), and were processed as described above for the first group with the only exception that the IE reperfusion was done with a sample oxygenated cardioplegic composition as shown in TABLE I, which had been cooled to 25° C. prior to commencing the reperfusion process.

Seven pigs were assigned to the third group ("normothermic" group), and were processed as described above for the first group with the only exception that the IE reperfusion was done with a sample oxygenated cardioplegic composition as shown in TABLE I, which had been warmed to 35° C. prior to commencing the reperfusion process.

Figure 2:
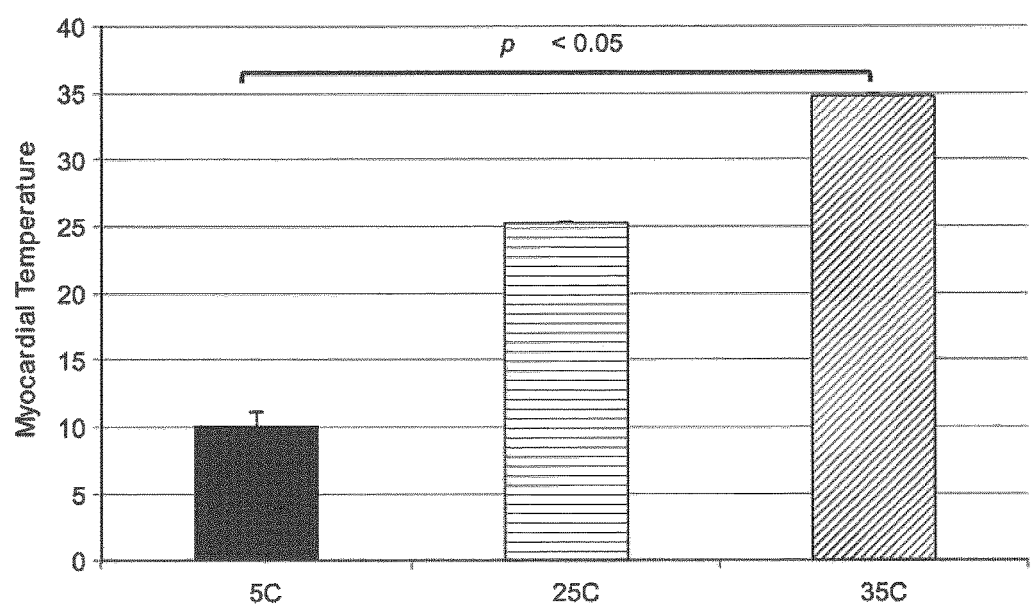
FIG. 2 is a chart showing the myocardial temperature achieved in harvested pig hearts after an initial 3-minute reperfusion period.

The data in FIG. 2 show that the myocardial temperatures recorded in the hearts receiving the IE reperfusion treatment with the sample oxygenated cardioplegic composition chilled to 5° C. dropped to about 10° C. by the end of the 3-minute IE reperfusion period. The myocardial temperatures recorded in the hearts that received IE reperfusion with the sample oxygenated cardioplegic composition cooled to 25° C. were about 25° C., while the myocardial temperatures recorded in the hearts that received reperfusion with the selected oxygenated cardioplegic composition were about 35° C.

Figure 3:
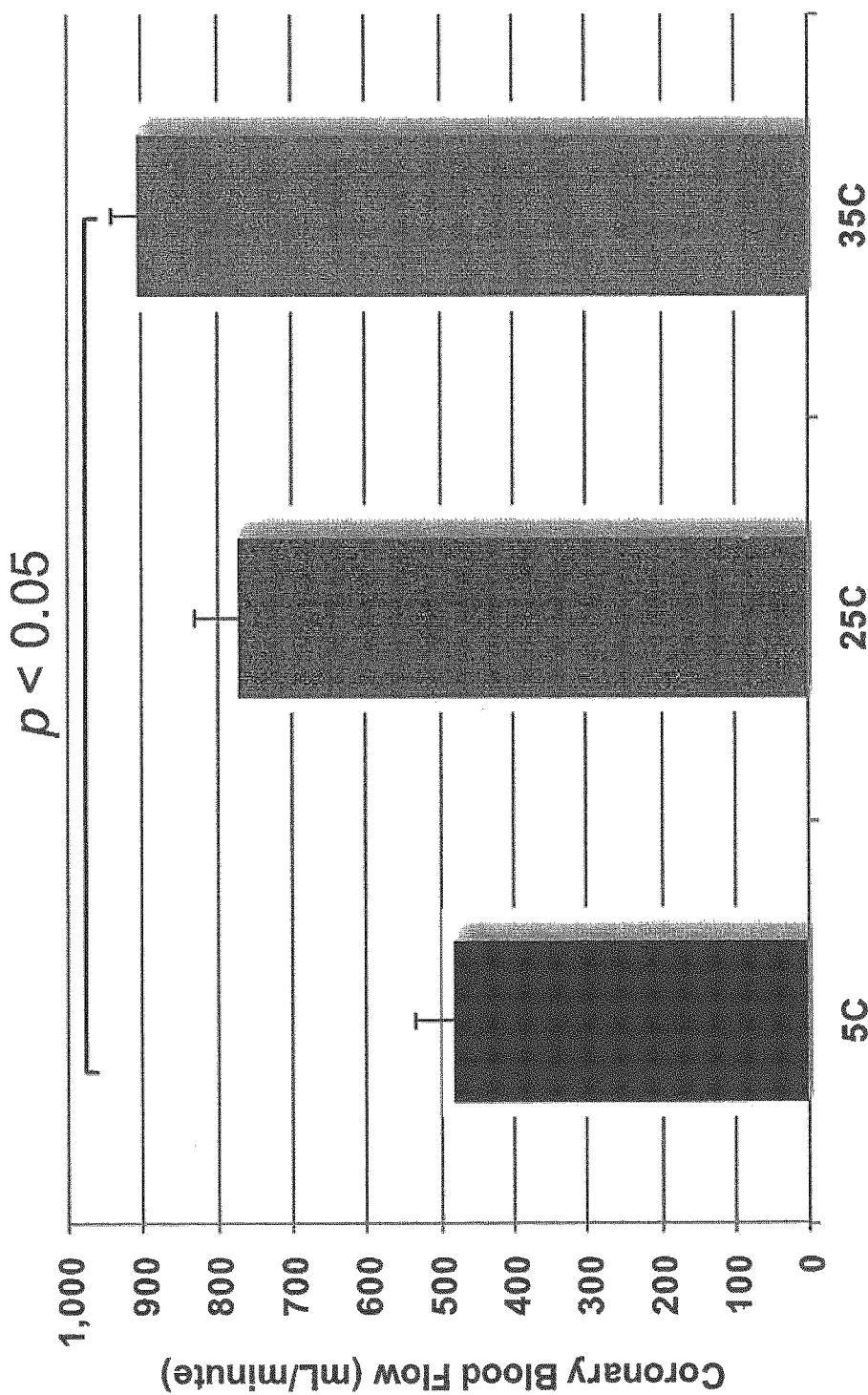
FIG. 3 is a chart showing the effect of reperfusate temperature on the coronary blood flow through harvested pig hearts, measured after the initial 3-minute reperfusion period.

FIG. 3 shows that rates of coronary blood flow were reduced by about 15% in hearts that were reperfused with the sample oxygenated cardioplegic composition cooled to 25° C. compared to coronary blood flow in hearts that received reperfusion with the sample oxygenated cardioplegic composition. However, rates of coronary blood flow were reduced by nearly 50% in hearts that were reperfused with the sample oxygenated cardioplegic composition chilled to 5° C. compared to coronary blood flow in hearts that received reperfusion with the sample oxygenated cardioplegic composition.

Figure 4:
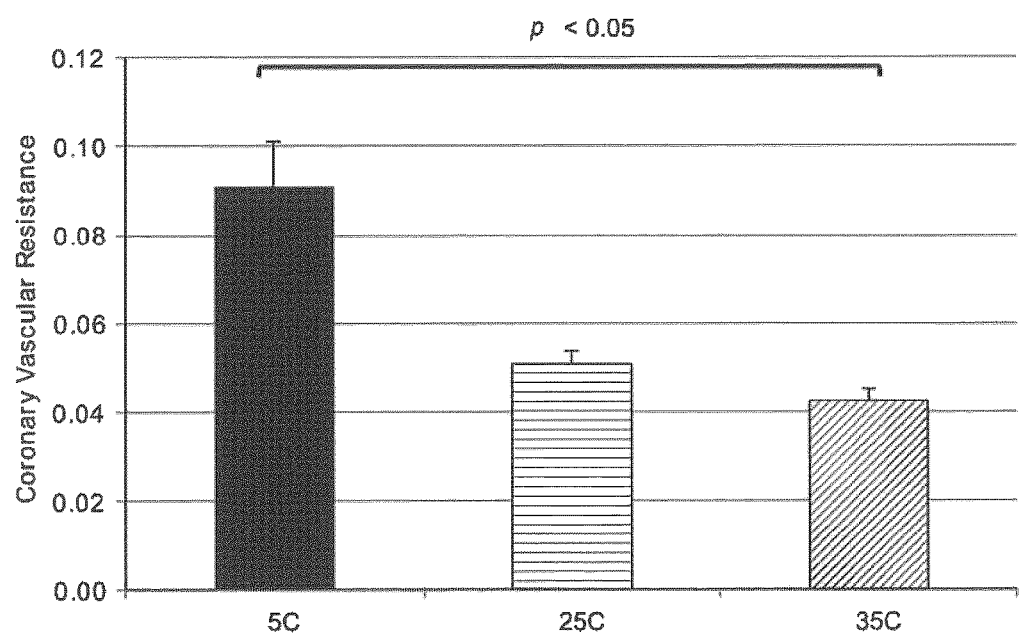
FIG. 4 is a chart showing the effect of reperfusate temperature on coronary vascular resistance to blood flow through harvested pig hearts, measured after the initial 3-minute reperfusion period.

FIG. 4 shows that the coronary vascular resistance in hearts reperfused with the cooled oxygenated cardioplegic composition dropped by about 40% compared to the hearts reperfused with the oxygenated cardioplegic composition, while the chilled oxygenated cardioplegic composition caused a reduction of more than 50% in the coronary vascular resistance.

Figure 5:
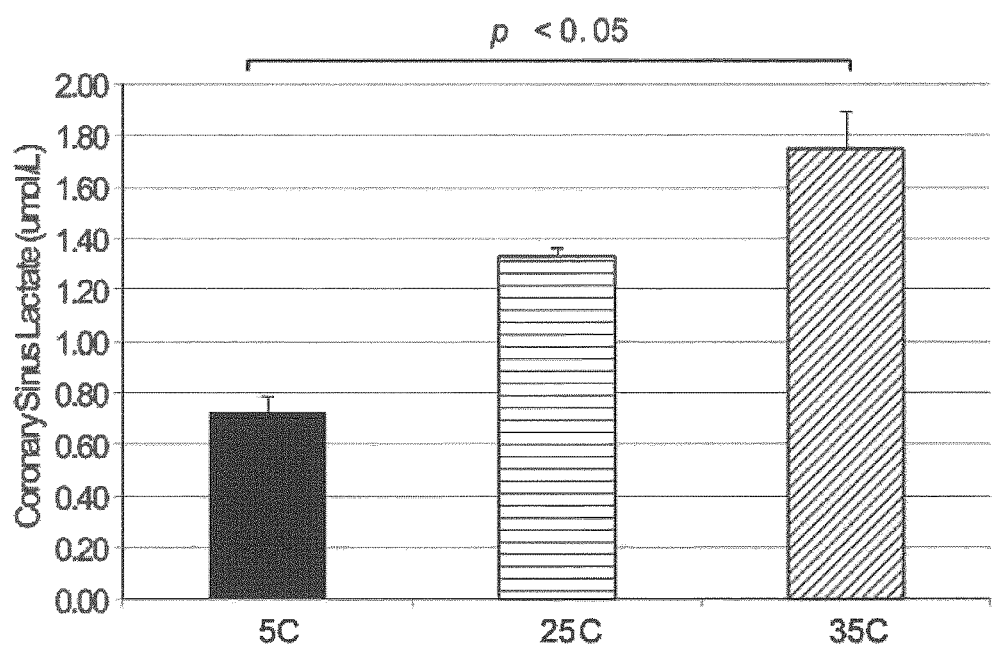
FIG. 5 is a chart showing the effect of reperfusate temperature on coronary sinus lactate washout from harvested pig hearts, measured after the initial 3-minute reperfusion period.

FIG. 5 shows that the coronary sinus lactate dropped by more than 50% in hearts that received the chilled IE reperfusion treatment, and by about 25% in hearts that received the cooled IE reperfusion treatment, when compared to the coronary sinus lactate levels in the hearts receiving the normothermic IE reperfusion treatment.

Figure 6:
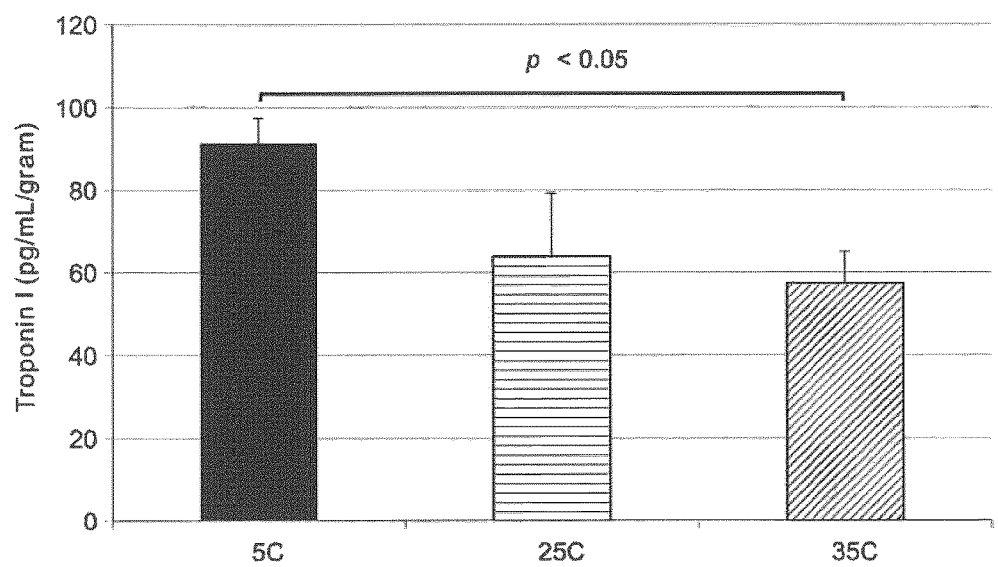
FIG. 6 is a chart showing the effect of reperfusate temperature on the accumulation of Troponin I (a marker of myocardial injury) in the perfusate solution, measured 5 hours after harvest of the pig hearts.

FIG. 6 shows that levels of Troponin I (a marker for myocardial injury) increased as the temperature of the IE reperfusion temperature decreased, relative to the levels observed in hearts receiving the normothermic IE reperfusion treatment.

Figure 7:
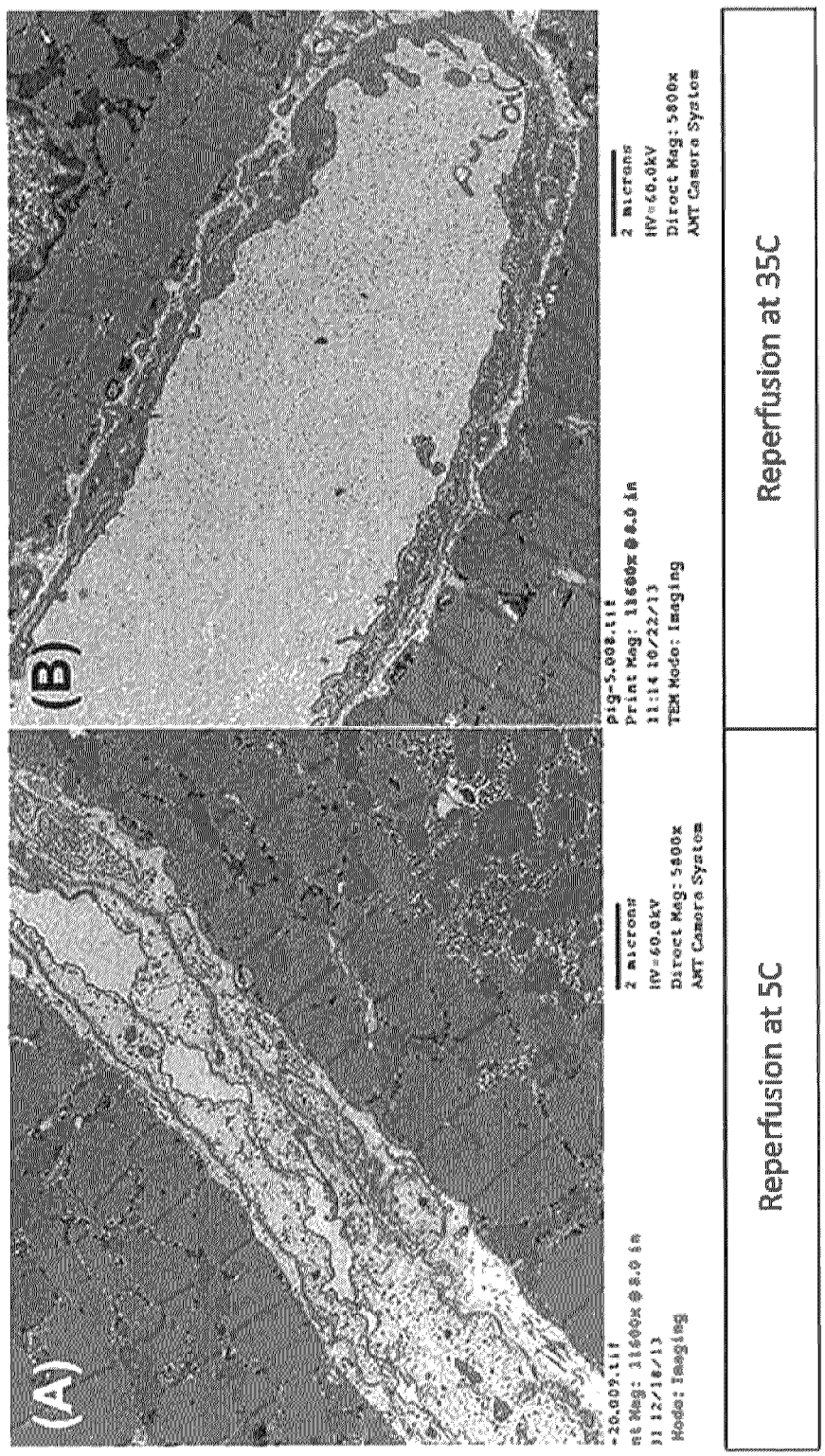

FIG. 7(A) is an electron micrograph showing a swollen endothelial cell in a capillary of a heart that received the chilled IE reperfusion treatment for 3 minutes, while FIG. 7(B) is an electron micrograph showing a typical normal-appearing endothelial cell in a capillary of a heart that received the normothermic IE reperfusion treatment for 3 minutes.

Figure 8:
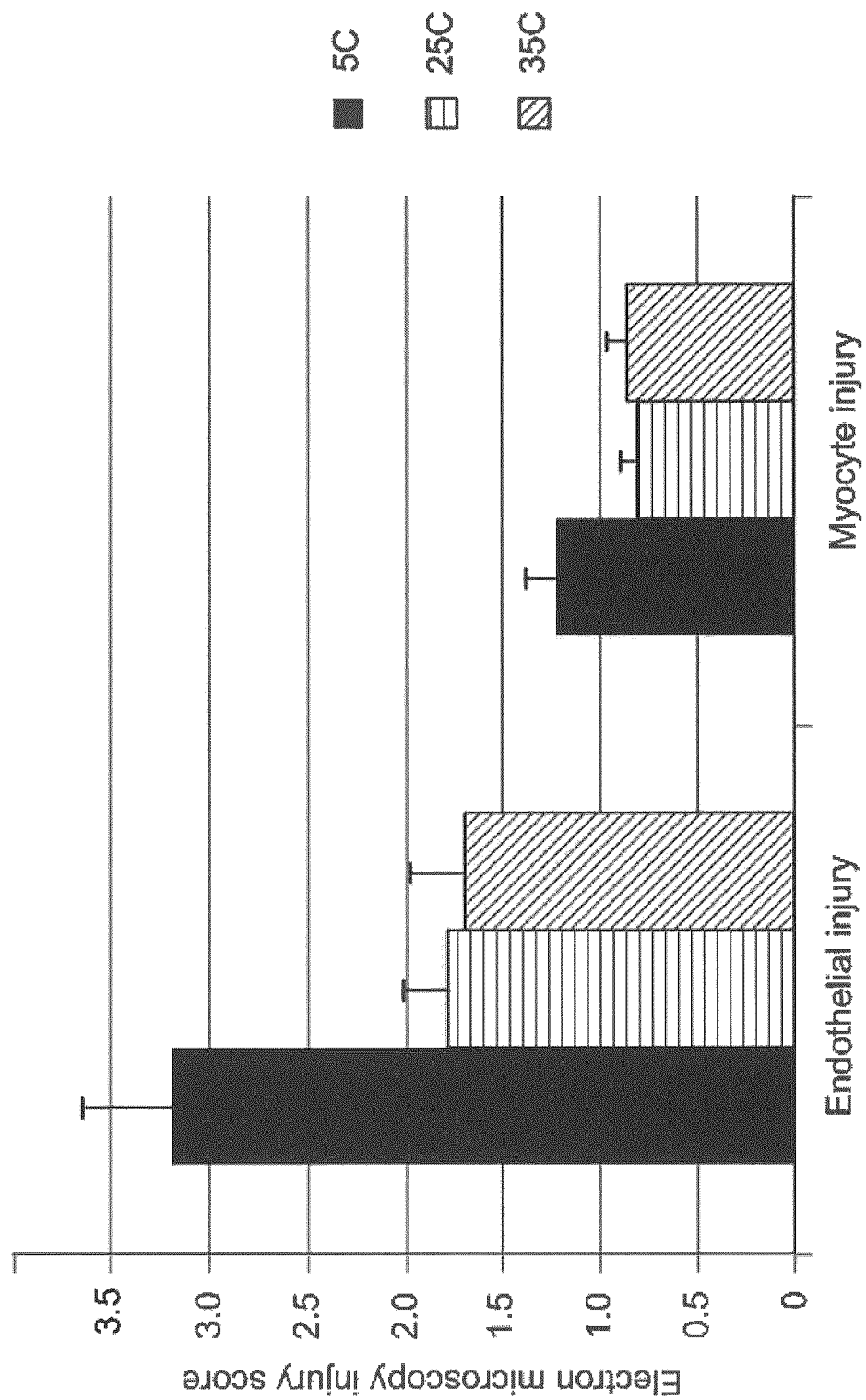
FIG. 8 is a chart presenting the average extent of injury to endothelial cells and myocytes in harvested pig hearts, as observed in electron-microscopy micrographs and scored with a scoring system, as a function of reperfusion temperature.

FIG. 8 is a chart comparing the scores of endothelial injury and myocyte injury from hearts receiving chilled IE reperfusion for three minutes and from hearts receiving normothermic IE reperfusion for three minutes.

Figure 9:
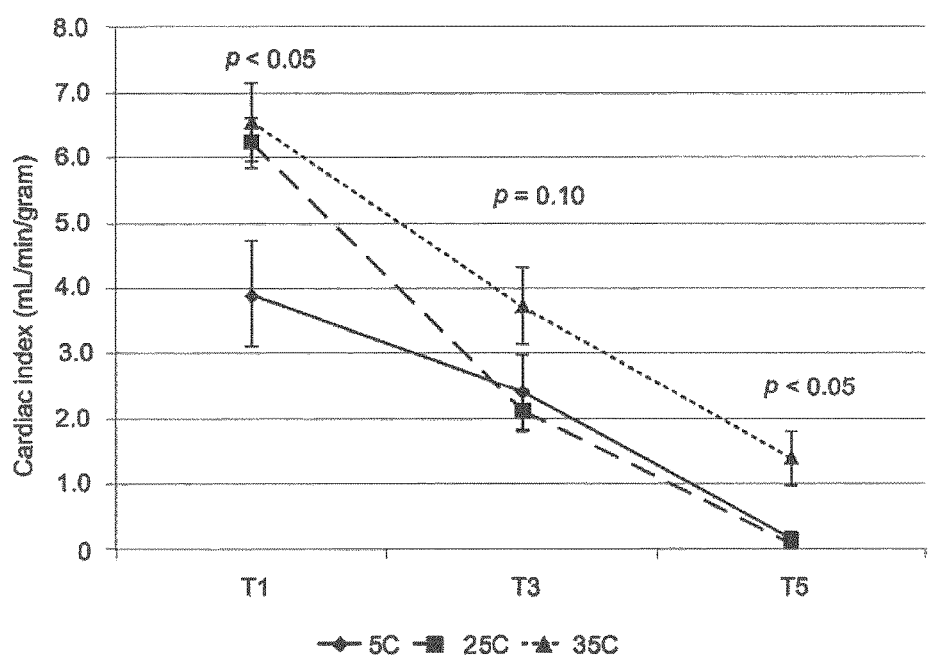
FIG. 9 is a chart showing the effect of reperfusate temperature on the cardiac index of harvested pig hearts, measured 1 hour ("T1"), 3 hours ("T3"), and 5 hours ("T5") after harvest of the pig hearts.

FIG. 9 is a chart showing the effects on cardiac indices of IE reperfusion with a cooled oxygenated cardioplegic composition and with a chilled oxygenated cardioplegic composition, with the effects of IP perfusion with a normothermic oxygenated cardioplegic composition.

Figure 10:
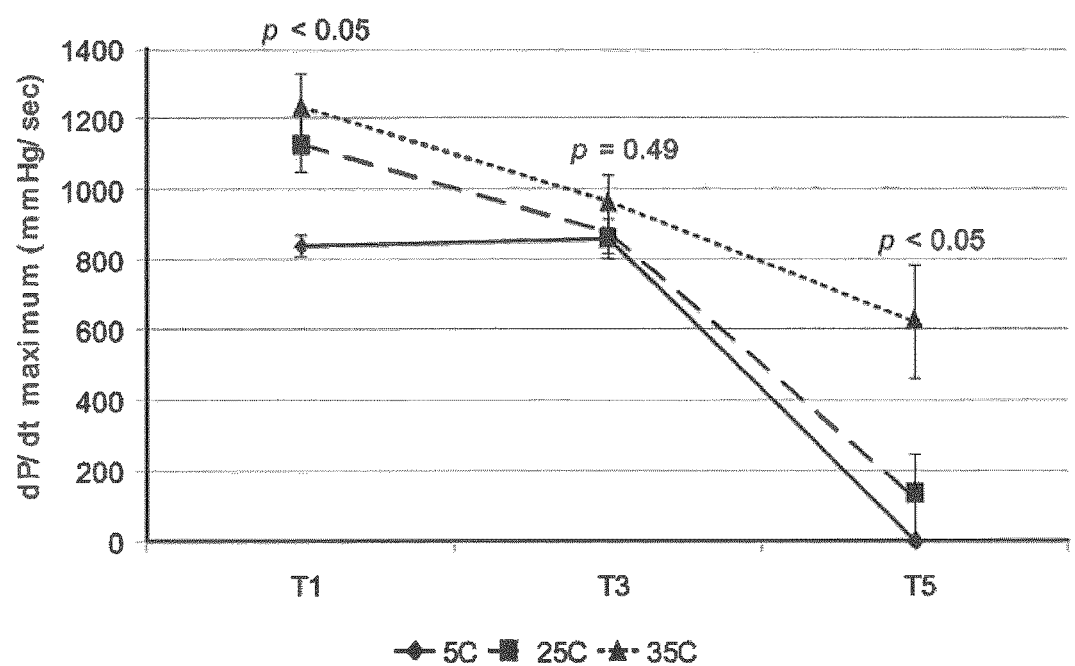
FIG. 10 is a chart showing the effect of reperfusate temperature on the systolic function of harvested pig hearts, measured 1 hour ("T1"), 3 hours ("T3"), and 5 hours ("T5") after harvest of the pig hearts.

FIG. 10 is a chart comparing the effects of the initial IE reperfusion temperatures on the subsequent systolic functioning of harvested hearts after 1 hour ("T1"), 3 hours ("T3"), and 5 hours ("T5") of resuscitation and perfusion of the hearts with the blood-STEEN solution mixture.

Figure 11:
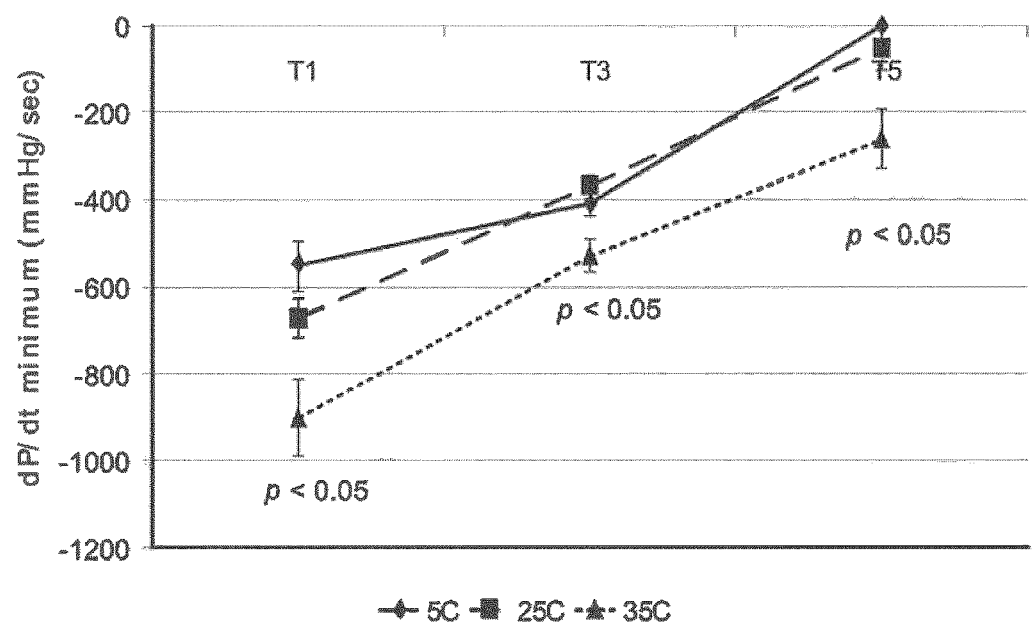
FIG. 11 is a chart showing the effect of reperfusate temperature on the diastolic function of harvested pig hearts, measured 1 hour ("T1"), 3 hours ("T3"), and 5 hours ("T5") after harvest of the pig hearts.

FIG. 11 is a chart comparing the effects of the initial IE reperfusion temperatures on the subsequent diastolic functioning of harvested after 1 hour ("T1"), 3 hours ("T3"), and 5 hours ("T5") of resuscitation and perfusion of the hearts with the blood-STEEN solution mixture.

The data collected in this study demonstrate that the initial reperfusion conditions, which last only 3 minutes, significantly impact the severity of post-harvest trauma and the functional recovery of hearts harvested from porcine DCD donors.

Example 2

Figure 12:
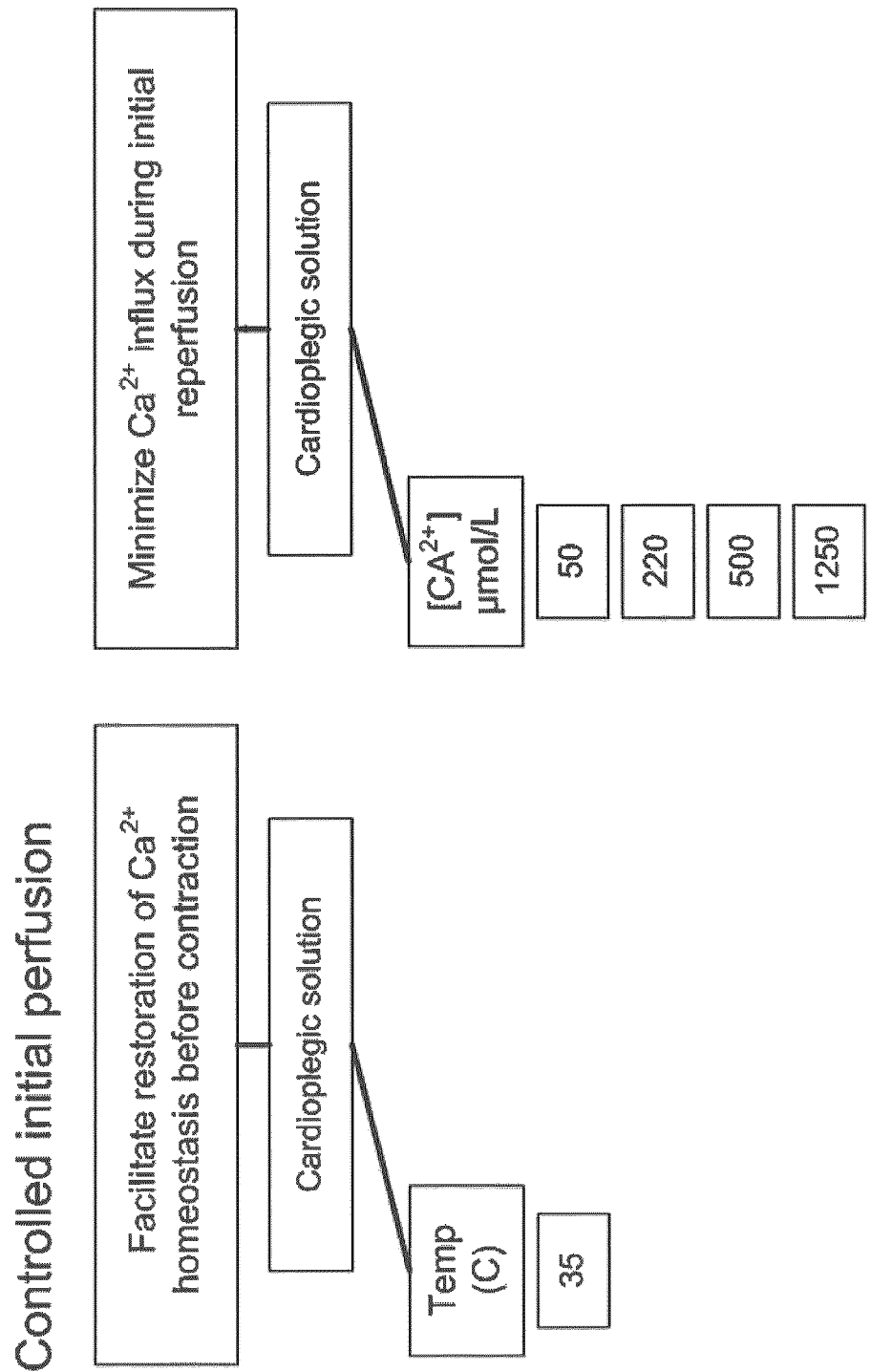
FIG. 12 is a schematic chart outlining the temperatures and $Ca^{2+}$ ion concentrations of the cardioplegic solutions used in Example 2.

The second study assessed the effects of reducing the $Ca^{2+}$ ion concentration in cardioplegic solutions to determine if lowering the $Ca^{2+}$ ion levels on the outside of myocytes would minimize the reverse mode functioning of the $Na^+$/$Ca^{2+}$ pump thereby reducing the accumulation of $Ca^{2+}$ ions within the myocytes. Accordingly, this study assessed the effects of 50 µmol/L, 220 µmol/L, 500 µmol/L, and 1250 µmol/L of $Ca^{2+}$ ions in sample oxygenated cardioplegic solutions (FIG. 12). The components of these sample solutions are shown in TABLE II. The sample solutions were also prepared at room temperature and their stated pH values were measured at room temperature, as for sample solutions in Example I but with different calcium chloride concentrations at 0.05, 0.22, 0.5, or 1.25 mmol/L respectively. All reperfusions in this example were done at 35° C.

TABLE II

| Sample II—Cardioplegic solutions (pH = 7.35) | | |
|---|---|---|
| Constituent | mmol/L | IU/L |
| Adenosine | 0.4 | |
| Lidocaine | 0.5 | |
| Glucose | 10 | |
| NaCl | 111.8 | |
| KCl | 5.9 | |

TABLE II-continued

Sample II—Cardioplegic solutions (pH = 7.35)

| Constituent | mmol/L | IU/L |
|---|---|---|
| NaHCO₃ | 32 | |
| NaH₂PO₄ | 1.2 | |
| CaCl₂ | varied | |
| MgCl₂ | 2.6 | |
| D-Mannitol | 120 | |
| Pyruvate | 1 | |
| Reduced glutathione | 3 | |
| Insulin | | 10 |

Figure 13:
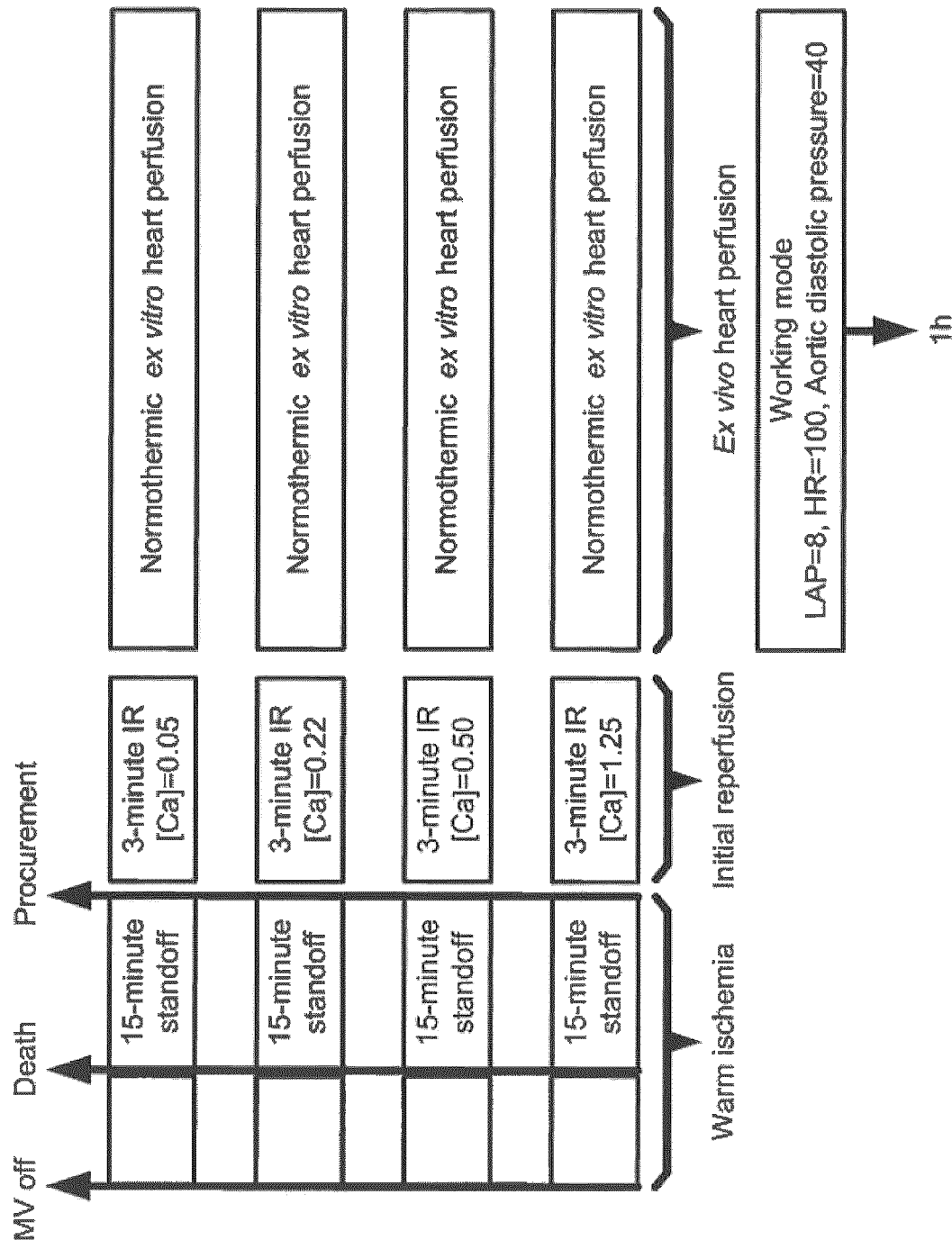
FIG. 13 is a schematic flowchart outlining the experimental protocols used in Example 2.

Twenty four pigs were separated into four groups and then euthanized following standard protocols and medical ethics procedures following the schematic flowchart shown in FIG. 13. Immediately after procurement of each heart was completed, each heart was installed into a Quest MPS®2 Myocardial Protection System. The harvested hearts from the first group of pigs were perfused for 3 minutes with a sample oxygenated cardioplegic composition containing 50 µmol/L $Ca^{2+}$ ions, which was warmed to 35° C. prior to commencing the reperfusion process. The harvested hearts from the second group of pigs were perfused for 3 minutes with the sample oxygenated cardioplegic composition containing 220 µmol/L $Ca^{2+}$ ions, which was warmed to 35° C. prior to commencing the reperfusion process. The harvested hearts from the third group of pigs were perfused for 3 minutes with the sample oxygenated cardioplegic composition containing 500 µmol/L $Ca^{2+}$ ions, which was warmed to 35° C. prior to commencing the reperfusion process. The harvested hearts from the fourth group of pigs were perfused for 3 minutes with the sample oxygenated cardioplegic composition containing 1,250 µmol/L $Ca^{2+}$ ions, which was warmed to 35° C. prior to commencing the reperfusion process.

The aortic perfusion pressure, coronary artery flow, and myocardial temperature were constantly monitored and recorded by the MPS®2 apparatus during the 3-minute initial reperfusion period. Blood gas samples were measured at 0, 30, 60, 120, and 180 seconds of the initial reperfusion period to collect data pertaining to changes occurring the partial pressure of $O_2$ ($PaO_2$), partial pressure of $CO_2$ ($PaCO_2$), pH levels, electrolyte levels, lactate levels among others.

After the initial 3-minute reperfusion period was completed. Each heart was removed from the Quest MPS®2 apparatus and transferred into an ex vivo heart perfusion (EVHP) apparatus where it was perfused with a constantly flowing supply of a blood-STEEN solution mixture (Hb 45 g/L; XVIVO Perfusion Inc., Englewood, Colo., USA) wherein its systolic function was restored and maintained in a Langendorff mode at a normothermic temperature of 35° C. for 1 hour. The aortic pressure and heart rate were constantly monitored and processed using the LAB-CHART® software. At 1 hour of perfusion with the blood-STEEN solution mixture in the EVHP apparatus, each heart was transitioned from the Langendorff mode to a working mode by bringing the left atrial pressure from 0 to 8 mmHg and pacing the heart at 100 bpm. Cardiac output, coronary blood flow, aortic root, and coronary sinus blood gases were measured, and cardiac function was assessed with a pressure-volume loop catheter. After these measurements were completed, each heart was immediately returned to the Langendorff mode.

Figure 14:
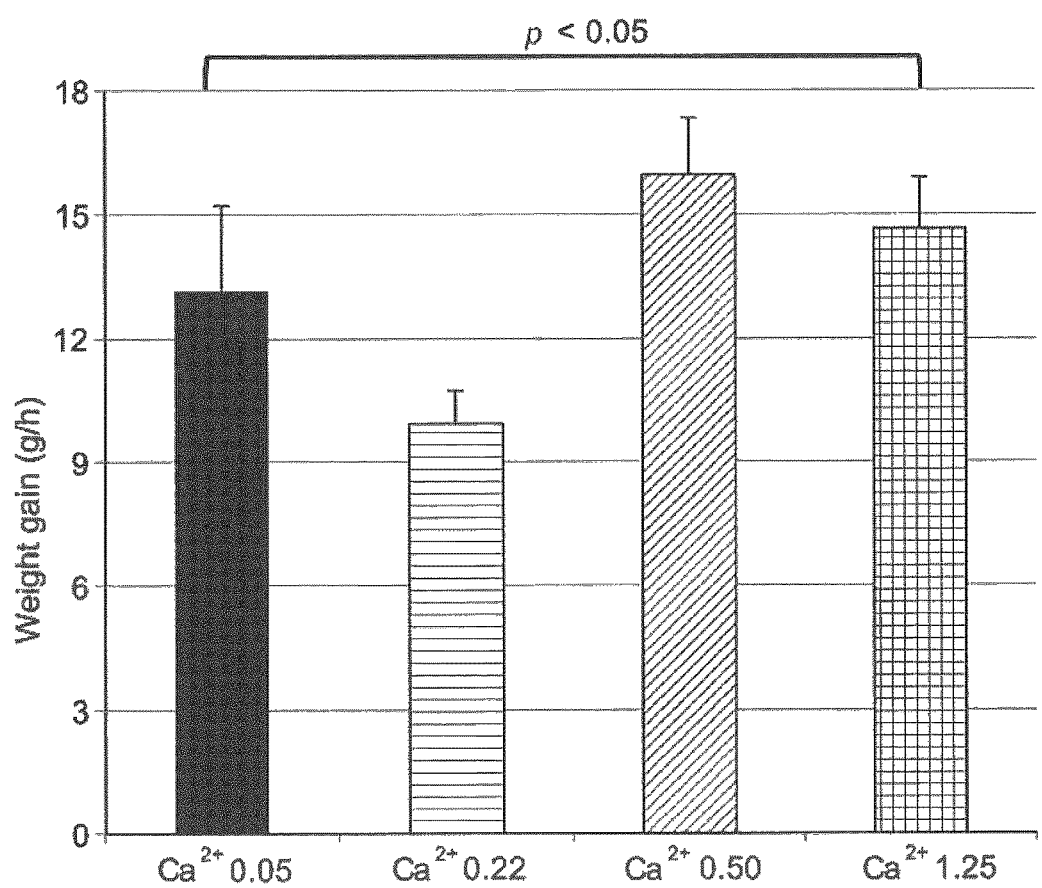
FIG. 14 is a chart showing the effect of $Ca^{2+}$ ion concentration in the reperfusate on weight gain in harvested pig hearts measured 1 hour after harvest.

FIG. 14 shows that the hearts initially reperfused at 35° C. with the sample oxygenated cardioplegic composition containing 220 µmol/L $Ca^{2+}$ ions developed significantly less myocardial edema than the hearts reperfused with oxygenated cardioplegic compositions containing one of the other three $Ca^{2+}$ ion concentrations.

Figure 15:
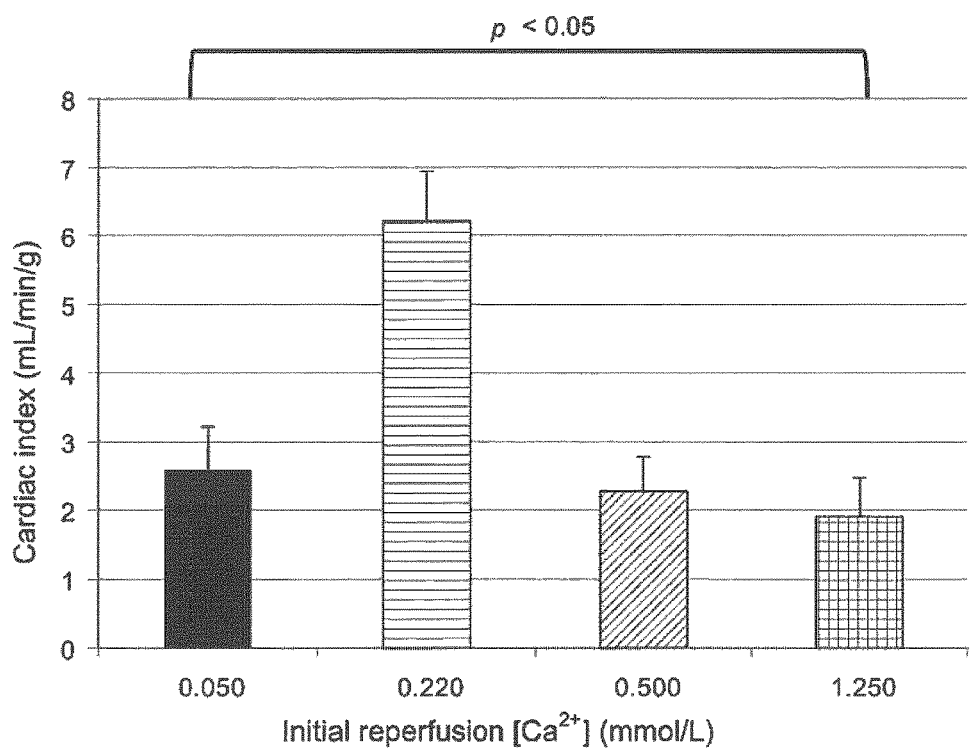
FIG. 15 is a chart showing the effect of $Ca^{2+}$ ion concentration in the reperfusate on the cardiac output of harvested pig hearts measured 1 hour after harvest.

FIG. 15 shows that the cardiac output (indexed for heart weight) of reperfused hearts improved as the $Ca^{2+}$ ion concentration in the oxygenated cardioplegic compositions was reduced from 1,250 µmol/L to 500 µmol/L to 220 µmol/L. However, the cardiac output of hearts reperfused with an oxygenated cardioplegic composition containing 50 µmol/L $Ca^{2+}$ ions was very poor.

Figure 16:
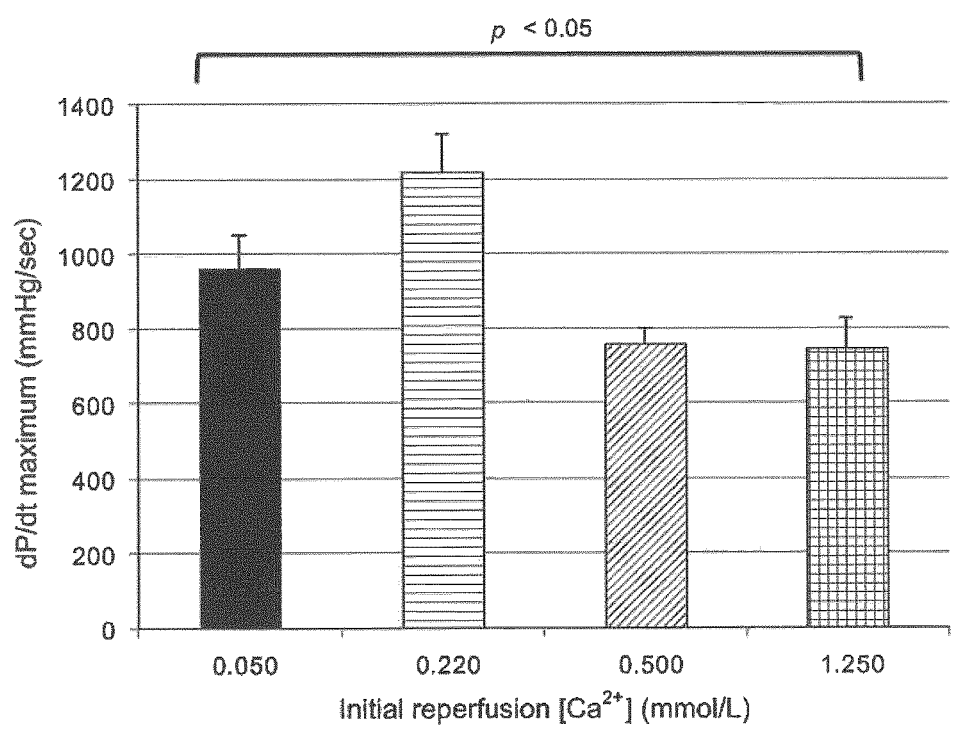
FIG. 16 is a chart showing the effect of $Ca^{2+}$ ion concentration on the contractility of the left ventricle during systole in harvested pig hearts, measured 1 hour after harvest.

FIG. 16 shows that the contractility of the left ventricle (as measured by dP/dt max) during systole in reperfused hearts improved as the $Ca^{2+}$ ion concentration in the oxygenated cardioplegic compositions was reduced from 1,250 µmol/L to 500 µmol/L to 220 µmol/L. However, contractility of the left ventricle in hearts reperfused with the oxygenated cardioplegic composition containing 50 µmol/L $Ca^{2+}$ ions was very poor.

Figure 17:
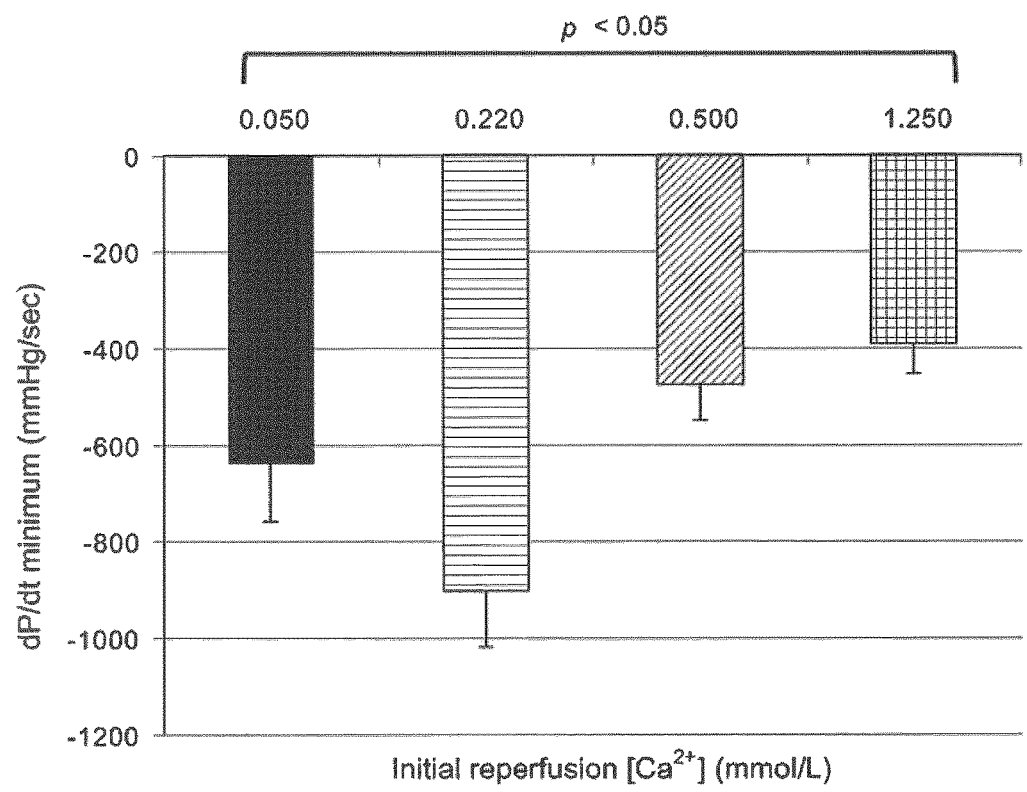
FIG. 17 is a chart showing the effect of $Ca^{2+}$ ion concentration on relaxation of the left ventricle during diastole in harvested pig hearts, measured 1 hour after harvest.

FIG. 17 shows that the relaxation of the left ventricle (as measured by dP/dt min) during diastole in reperfused hearts improved as the $Ca^{2+}$ ion concentration in the oxygenated cardioplegic compositions was reduced from 1,250 µmol/L to 500 µmol/L to 220 µmol/L. However, relaxation of the left ventricle in hearts reperfused with the oxygenated cardioplegic composition containing 50 µmol/L $Ca^{2+}$ ions was very poor.

The data collected during this study demonstrate that hypocalcemic oxygenated cardioplegic compositions at 35° C. significantly improved myocardial functional recovery. The best performance in this study was with a $Ca^{2+}$ ion concentration of 220 µmol/L. However, it appears that reducing the $Ca^{2+}$ ion concentration too low, for instance to 50 µmol/L, may have detrimental effects, a phenomenon previously described as the "calcium paradox".

Example 3

The next study assessed if there were potential incremental benefits to acidification of a hypocalcemic oxygenated cardioplegic composition. Accordingly, this study assessed the effects of adjusting the pH of sample hypocalcemic oxygenated cardioplegic compositions from 7.9 to 7.4, to 6.9, and to 6.4.

The components of these sample solutions IIIA to IIID are shown in TABLEs IIIA to IIID respectively.

TABLE IIIA

Sample IIIA—Cardioplegic solution (pH = 7.9)

| Constituent | mmol/L | IU/L |
|---|---|---|
| Adenosine | 0.4 | |
| Lidocaine | 0.5 | |
| Glucose | 10 | |
| NaCl | 43.8 | |
| KCl | 5.9 | |
| NaHCO₃ | 100 | |
| NaH₂PO₄ | 1.2 | |
| CaCl₂ | 0.22 | |
| MgCl₂ | 2.6 | |
| D-Mannitol | 120 | |
| Pyruvate | 1 | |
| Reduced glutathione | 3 | |
| Insulin | | 10 |

TABLE IIIB

Sample IIIB—Cardioplegic solution (pH = 7.35)

| Constituent | mmol/L | IU/L |
|---|---|---|
| Adenosine | 0.4 | |
| Lidocaine | 0.5 | |
| Glucose | 10 | |
| NaCl | 111.8 | |
| KCl | 5.9 | |
| NaHCO$_3$ | 32 | |
| NaH$_2$PO$_4$ | 1.2 | |
| CaCl$_2$ | 0.22 | |
| MgCl$_2$ | 2.6 | |
| D-Mannitol | 120 | |
| Pyruvate | 1 | |
| Reduced glutathione | 3 | |
| Insulin | | 10 |

TABLE IIIC

Sample IIIC—Cardioplegic solution (pH = 6.9)

| Constituent | mmol/L | IU/L |
|---|---|---|
| Adenosine | 0.4 | |
| Lidocaine | 0.5 | |
| Glucose | 10 | |
| NaCl | 131.8 | |
| KCl | 5.9 | |
| NaHCO$_3$ | 12 | |
| NaH$_2$PO$_4$ | 1.2 | |
| CaCl$_2$ | 0.22 | |
| MgCl$_2$ | 2.6 | |
| D-Mannitol | 120 | |
| Pyruvate | 1 | |
| Reduced glutathione | 3 | |
| Insulin | | 10 |

TABLE IIID

Sample IIID—Cardioplegic solution (pH = 6.4)

| Constituent | mmol/L | IU/L |
|---|---|---|
| Adenosine | 0.4 | |
| Lidocaine | 0.5 | |
| Glucose | 10 | |
| NaCl | 137.8 | |
| KCl | 5.9 | |
| NaHCO$_3$ | 6 | |
| NaH$_2$PO$_4$ | 1.2 | |
| CaCl$_2$ | 0.22 | |
| MgCl$_2$ | 2.6 | |
| D-Mannitol | 120 | |
| Pyruvate | 1 | |
| Reduced glutathione | 3 | |
| Insulin | | 10 |

Figure 18:
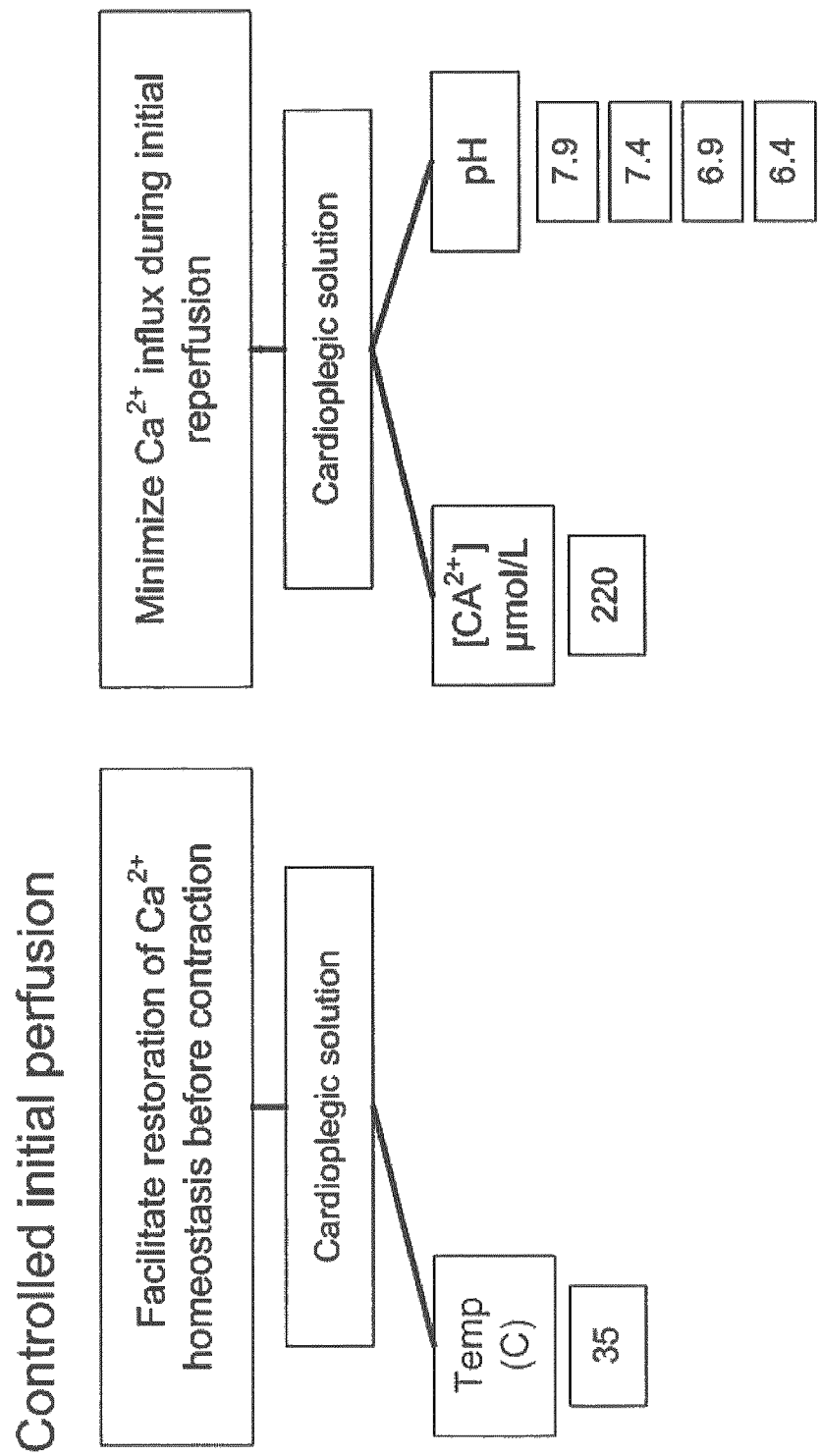
FIG. 18 is a schematic chart outlining the temperatures, $Ca^{2+}$ ion concentrations, and pH values of the cardioplegic solutions used in Example 3.

The sample cardioplegic solutions contained 220 µmol/L of Ca$^{2+}$ ions and all reperfusions were done at 35° C. (FIG. 18).

Figure 19:
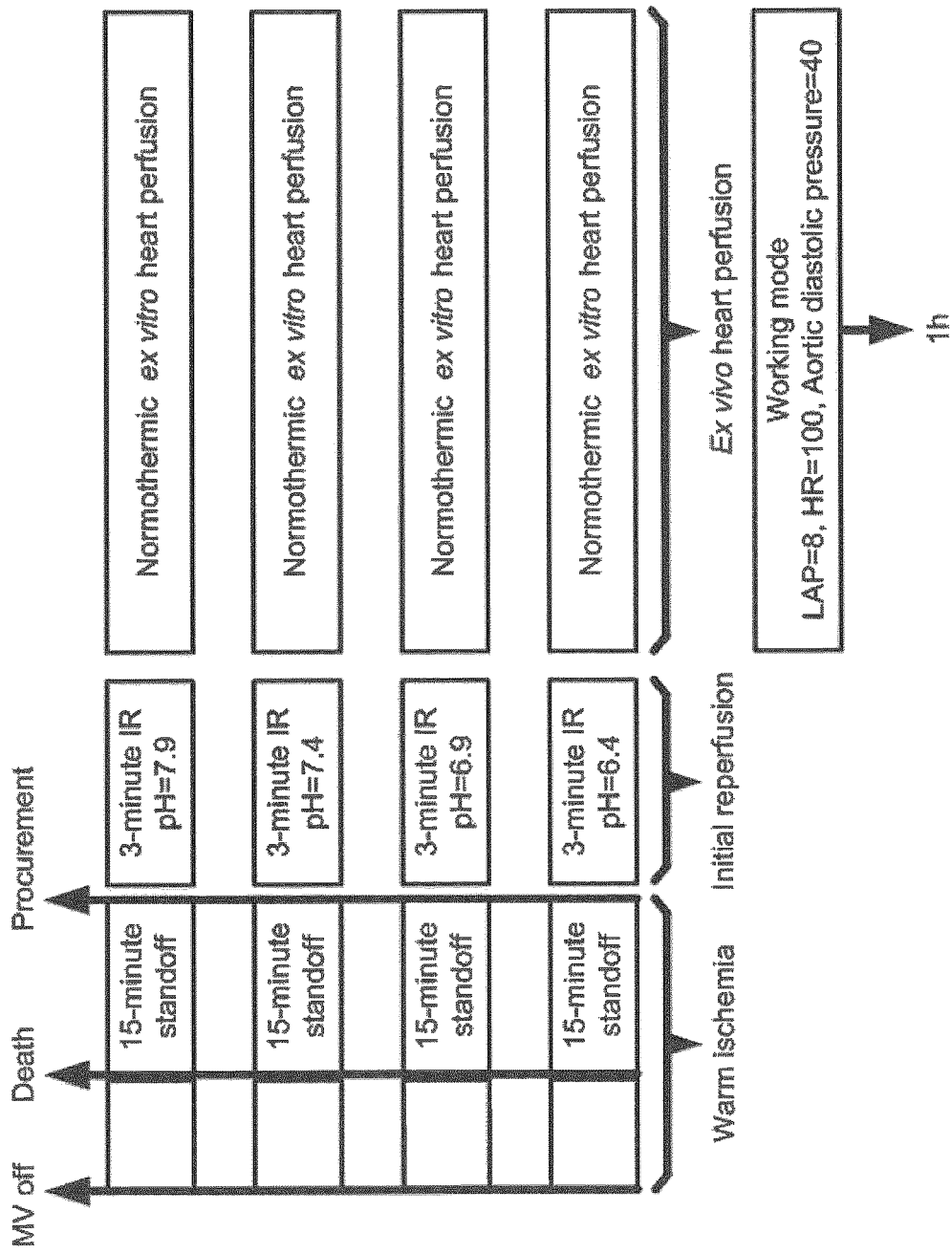
FIG. 19 is a schematic flowchart outlining the experimental protocols used in Example 3.

Twenty four pigs were separated into four groups and then euthanized following standard protocols and medical ethics procedures following the schematic flowchart shown in FIG. 19. Immediately after procurement of each heart was completed, each heart was installed into a Quest MPS®2 Myocardial Protection System. The harvested hearts from the first group of pigs were perfused for 3 minutes with the sample hypocalcemic oxygenated cardioplegic composition with a pH of 7.9, which was warmed to 35° C. prior to commencing the reperfusion process. The harvested hearts from the second group of pigs were perfused for 3 minutes with a sample hypocalcemic oxygenated cardioplegic composition adjusted to a pH of 7.4, which was warmed to 35° C. prior to commencing the reperfusion process. The harvested hearts from the third group of pigs were perfused for 3 minutes with a sample hypocalcemic oxygenated cardioplegic composition adjusted to a pH of 6.9, which was warmed to 35° C. prior to commencing the reperfusion process. The harvested hearts from the fourth group of pigs were perfused for 3 minutes with the sample hypocalcemic oxygenated cardioplegic composition adjusted to a pH of 6.4, which was warmed to 35° C. prior to commencing the reperfusion process.

The aortic perfusion pressure, coronary artery flow, and myocardial temperature were constantly monitored and recorded by the MPS®2 apparatus during the 3-minute initial reperfusion period. Blood gas samples were measured at 0, 30, 60, 120, and 180 seconds of the initial reperfusion period to collect data pertaining to changes occurring the partial pressure of O$_2$ (PaO$_2$), partial pressure of CO$_2$ (PaCO$_2$), pH levels, electrolyte levels, lactate levels among others.

After the initial 3-minute reperfusion period was completed. Each heart was removed from the Quest MPS®2 apparatus and transferred into an ex vivo heart perfusion (EVHP) apparatus where it was perfused with a constantly flowing supply of a blood-STEEN solution mixture (Hb 45 g/L; XVIVO Perfusion Inc., Englewood, Colo., USA) wherein its systolic function was restored and maintained in a Langendorff mode at a normothermic temperature of 35° C. for 1 hour. The aortic pressure and heart rate were constantly monitored and processed using the LAB-CHART® software. After 1 hour of perfusion with the blood-STEEN solution mixture in the EVHP apparatus, each heart was transitioned from the Langendorff mode to a working mode by bringing the left atrial pressure from 0 to 8 mmHg and pacing the heart at 100 bpm. Cardiac output, coronary blood flow, aortic root, and coronary sinus blood gases were measured, and cardiac function was assessed with a pressure-volume loop catheter. After these measurements were completed, each heart was immediately returned to the Langendorff mode.

Figure 20:
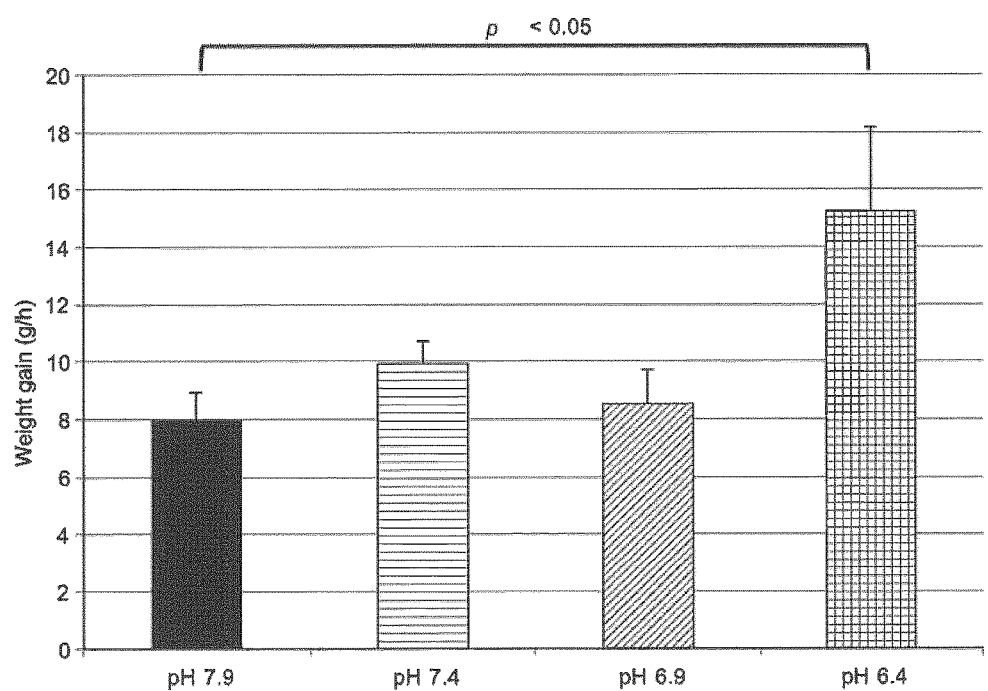
FIG. 20 is a chart showing the effect of pH of the cardioplegic reperfusate solution on weight gain in harvested pig hearts, measured 1 hour after harvest.

FIG. 20 shows that the hearts initially reperfused at 35° C. with the sample hypocalcemic oxygenated cardioplegic compositions that was mildly acidic (i.e., pH 6.4) exhibited more myocardial edema than those that were reperfused with the more alkaline (i.e., pH of 7.9, 7.4, 6.9) hypocalcemic oxygenated cardioplegic compositions.

Figure 21:
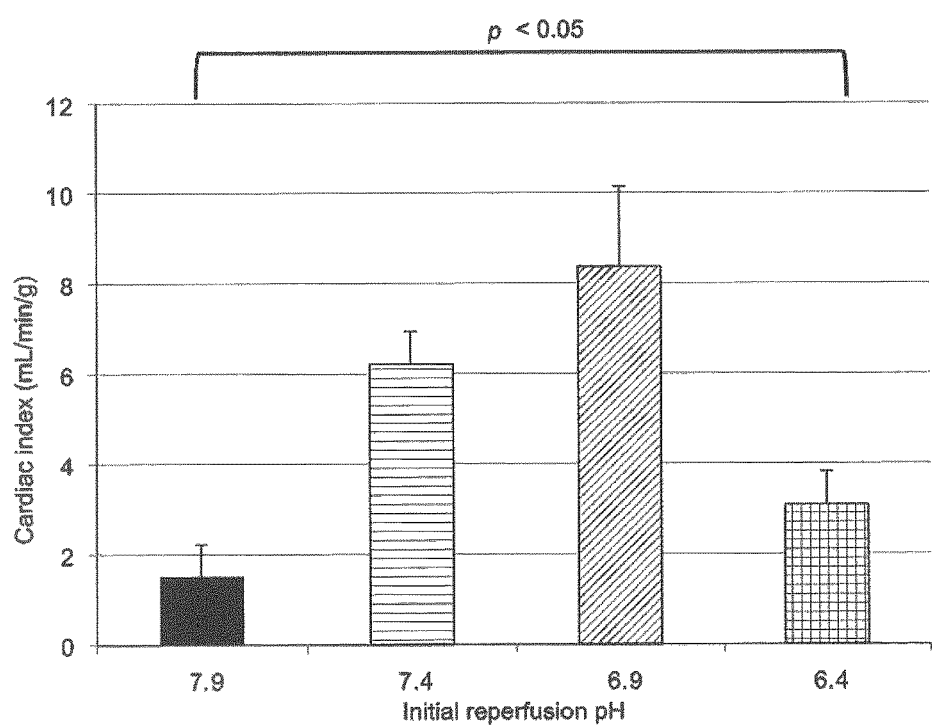
FIG. 21 is a chart showing the effect of pH of the cardioplegic reperfusate solution on the cardiac output of harvested pig hearts, measured 1 hour after harvest.

FIG. 21 shows that the cardiac outputs (indexed for heart weight) of reperfused hearts in a slightly acidic hypocalcemic oxygenated cardioplegic composition (i.e., pH 6.9) and a slightly alkaline hypocalcemic oxygenated cardioplegic composition (i.e., pH 7.4) were significantly better that the cardiac outputs of hearts reperfused in hypocalcemic oxygenated cardioplegic compositions adjusted to pH 7.9 or 6.4.

Figure 22:
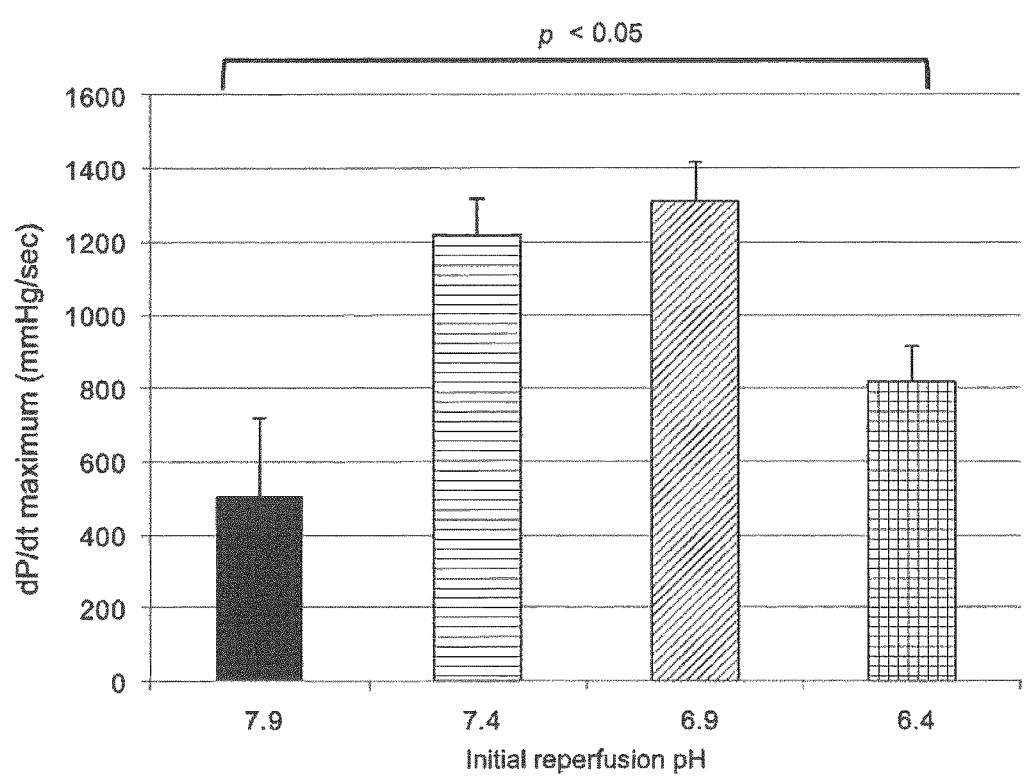
FIG. 22 is a chart showing the effect of pH of the cardioplegic reperfusate solution on the contractility of the left ventricle during systole in harvested pig hearts, measured 1 hour after harvest.

FIG. 22 shows that the contractility of the left ventricle (as measured by dP/dt max) during systole in reperfused hearts in a slightly acidic hypocalcemic oxygenated cardioplegic composition (i.e., pH 6.9) and a slightly alkaline hypocalcemic oxygenated cardioplegic composition (i.e., pH 7.4) were significantly better than the left ventricle contractility in hearts reperfused in hypocalcemic oxygenated cardioplegic compositions adjusted to pH 7.9 or 6.4.

Figure 23:
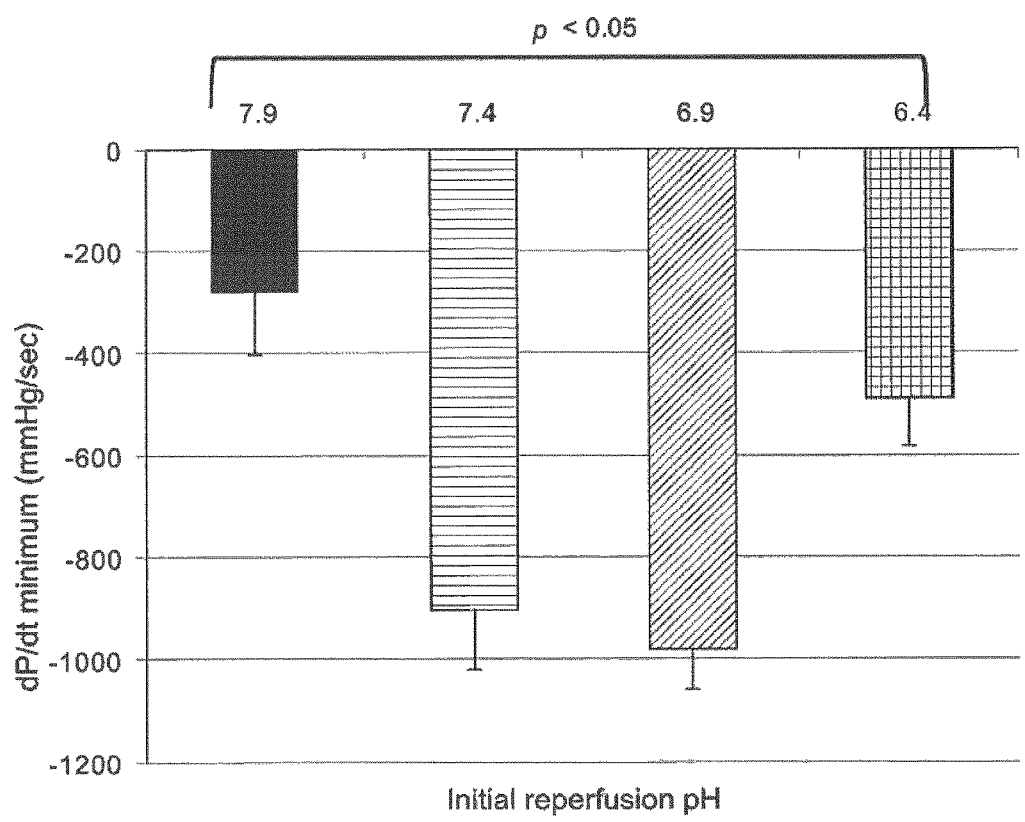
FIG. 23 is a chart showing the effect of pH of the cardioplegic reperfusate solution on relaxation of the left ventricle during diastole in harvested pig hearts, measured 1 hour after harvest.

FIG. 23 shows that the relaxation of the left ventricle (as measured by dP/dt min) during diastole in reperfused hearts in a slightly acidic hypocalcemic oxygenated cardioplegic composition (i.e., pH 6.9) and a slightly alkaline hypocalcemic oxygenated cardioplegic composition (i.e., pH 7.4)

were significantly better than the left ventricle relaxation in hearts reperfused in hypocalcemic oxygenated cardioplegic compositions adjusted to pH 7.9 or 6.4.

The data collected during this study demonstrate that initial alkaline reperfusion is detrimental and significant acidity (e.g., pH of 6.4) is also detrimental. However, it appears that mild acidosis (e.g. pH of 6.6 to 6.9) is beneficial.

Example 4

Part 1: The next study assessed if there were potential incremental benefits to increasing the duration of reperfusion of harvested donor hearts with a mildly acidic hypocalcemic oxygenated cardioplegic composition.

The sample solutions used for these tests were the same as Sample solutions IIIC described above.

Figure 24:
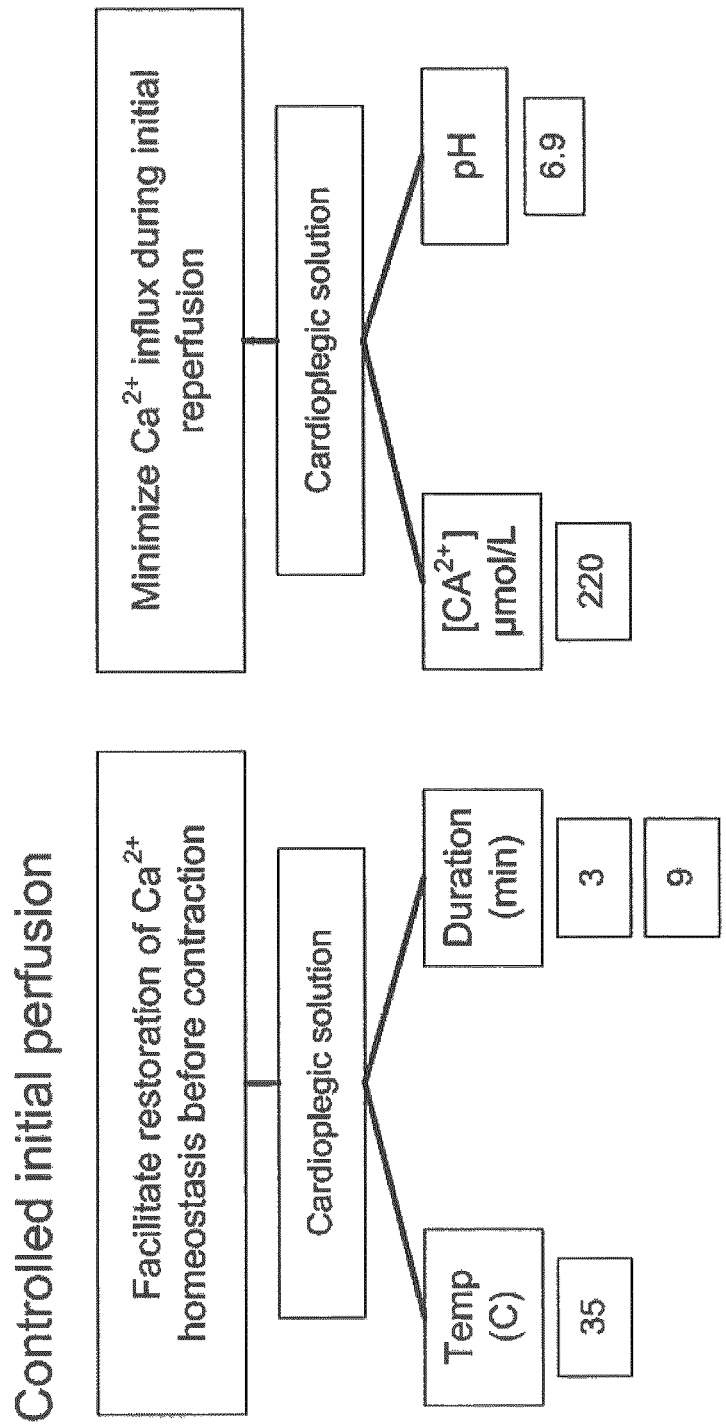
FIG. 24 is a schematic chart outlining the temperatures, $Ca^{2+}$ ion concentrations, and pH values of the cardioplegic reperfusate solutions, and the duration of reperfusion times used in Example 4.

Accordingly, this study assessed the effects of 3 minutes or 9 minutes reperfusion with a sample mildly acidic (pH 6.9) hypocalcemic (220 µmol/L $Ca^{2+}$) oxygenated cardioplegic solution at 35° C. (FIG. 24). The cardioplegic solution for Part 1 of this study contained 400 µmol/L adenosine and 500 µmol/L lidocaine.

Figure 25:
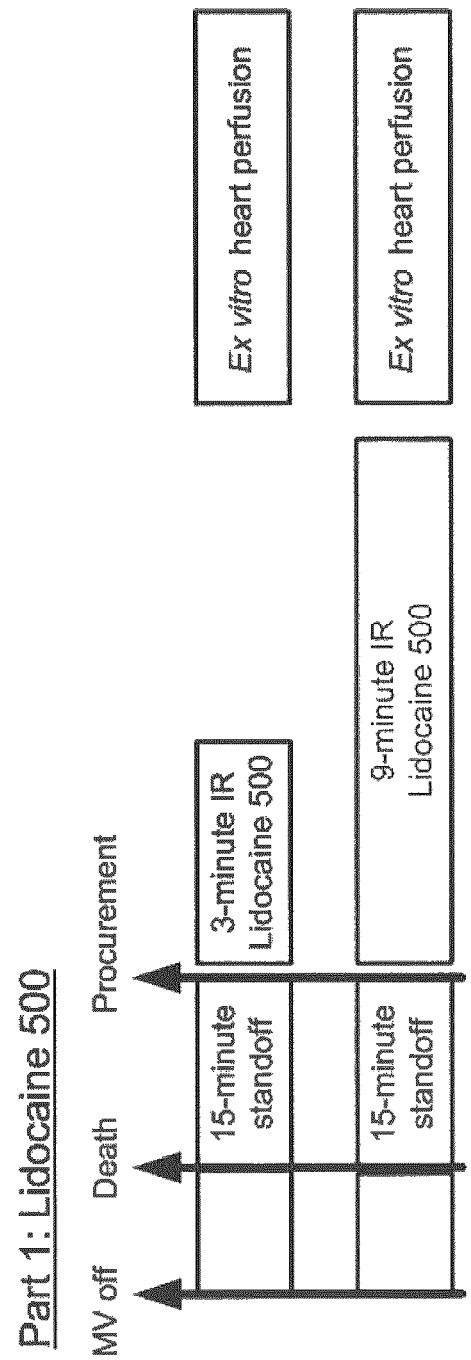
FIG. 25 is a schematic flowchart outlining the experimental protocols used in Example 4, Part 1.

Twelve pigs were separated into two groups and then euthanized following standard protocols and medical ethics procedures following the schematic flowchart shown in FIG. 25. Immediately after procurement of each heart was completed, each heart was installed into a Quest MPS®2 Myocardial Protection System. The harvested hearts from the first group of pigs were perfused for 3 minutes with the sample mildly acidic hypocalcemic oxygenated cardioplegic composition warmed to 35° C. prior to commencing the reperfusion process for 3 minutes. The harvested hearts from the second group of pigs were perfused for 9 minutes with the sample mildly acidic hypocalcemic oxygenated cardioplegic composition that was warmed to 35° C. prior to commencing the reperfusion process.

The aortic perfusion pressure, coronary artery flow, and myocardial temperature were constantly monitored and recorded by the MPS®2 apparatus during the 3-minute or 9-minute initial reperfusion period. Blood gas samples were measured at 0, 30, 60, 120, and 180 seconds of the initial reperfusion period to collect data pertaining to changes occurring the partial pressure of $O_2$ ($PaO_2$), partial pressure of $CO_2$ ($PaCO_2$), pH levels, electrolyte levels, lactate levels among others.

After the initial 3-minute reperfusion period or the initial 9-minute reperfusion period was completed, each heart was removed from the Quest MPS®2 apparatus and transferred into an ex vivo heart perfusion (EVHP) apparatus where it was perfused with a constantly flowing supply of a blood-STEEN solution mixture (Hb 45 g/L; XVIVO Perfusion Inc., Englewood, Colo., USA) wherein its systolic function was restored and maintained in a Langendorff mode at a normothermic temperature of 35° C. for 1 hour, 3 hours, and 5 hours. The aortic pressure and heart rate were constantly monitored and processed using the LABCHART® software. After 1 hour of perfusion with the blood-STEEN solution mixture in the EVHP apparatus, each heart was transitioned from the Langendorff mode to a working mode by bringing the left atrial pressure from 0 to 8 mmHg and pacing the heart at 100 bpm. Cardiac output, coronary blood flow, aortic root, and coronary sinus blood gases were measured, and cardiac function was assessed with a pressure-volume loop catheter. After these measurements were completed, each heart was immediately returned to the Langendorff mode for an additional 2 hours, after which the measurements were repeated (i.e., 3 hours after removal from reperfusion). After these measurements were completed, each heart was immediately returned to the Langendorff mode for an additional 2 hours, after which the measurements were repeated (i.e., 5 hours after removal from reperfusion).

Figure 26:
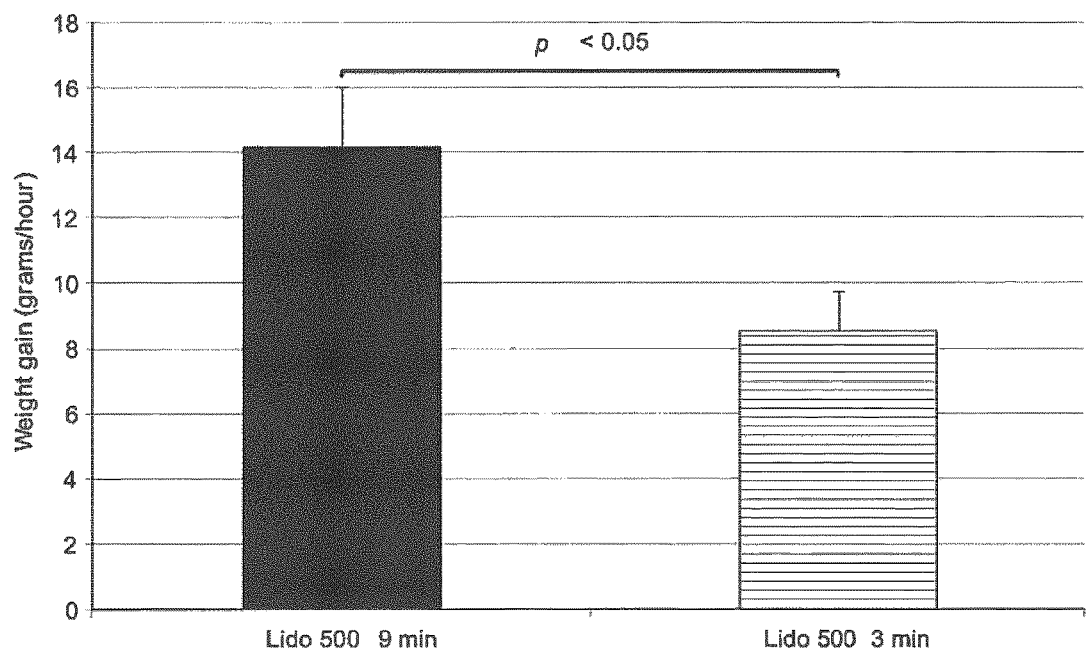
FIG. 26 is a chart showing the effect of duration of initial reperfusion on weight gain in harvested pig hearts.

FIG. 26 shows that the hearts initially reperfused for 9 minutes with the sample mildly acidic hypocalcemic oxygenated cardioplegic composition exhibited more myocardial edema than those that were reperfused for only 3 minutes.

Figure 27:
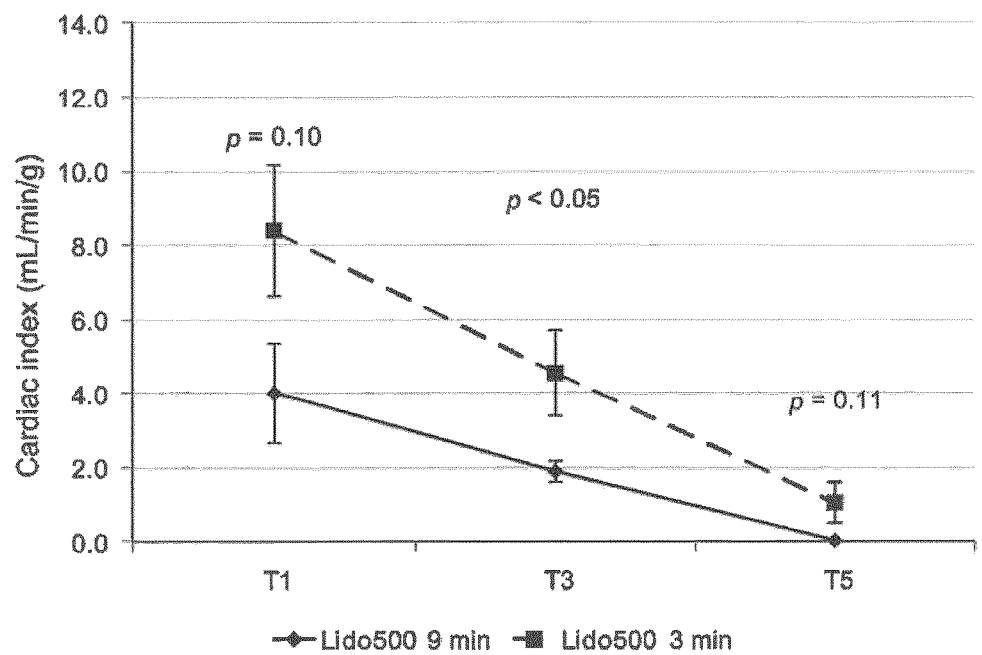
FIG. 27 is a chart showing the effects of duration of initial reperfusion on myocardial function of harvested pig hearts, measured 1 hour ("T1"), 3 hours ("T3"), and 5 hours ("T5") after harvest.

FIG. 27 shows that the hearts initially reperfused for 9 minutes trended toward worsening function as ex vivo heart perfusion proceeded from 1 hour to 3 hours to 5 hours.

These data suggest that the high (500 µmol/L) concentration of lidocaine might be toxic.

Figure 28:
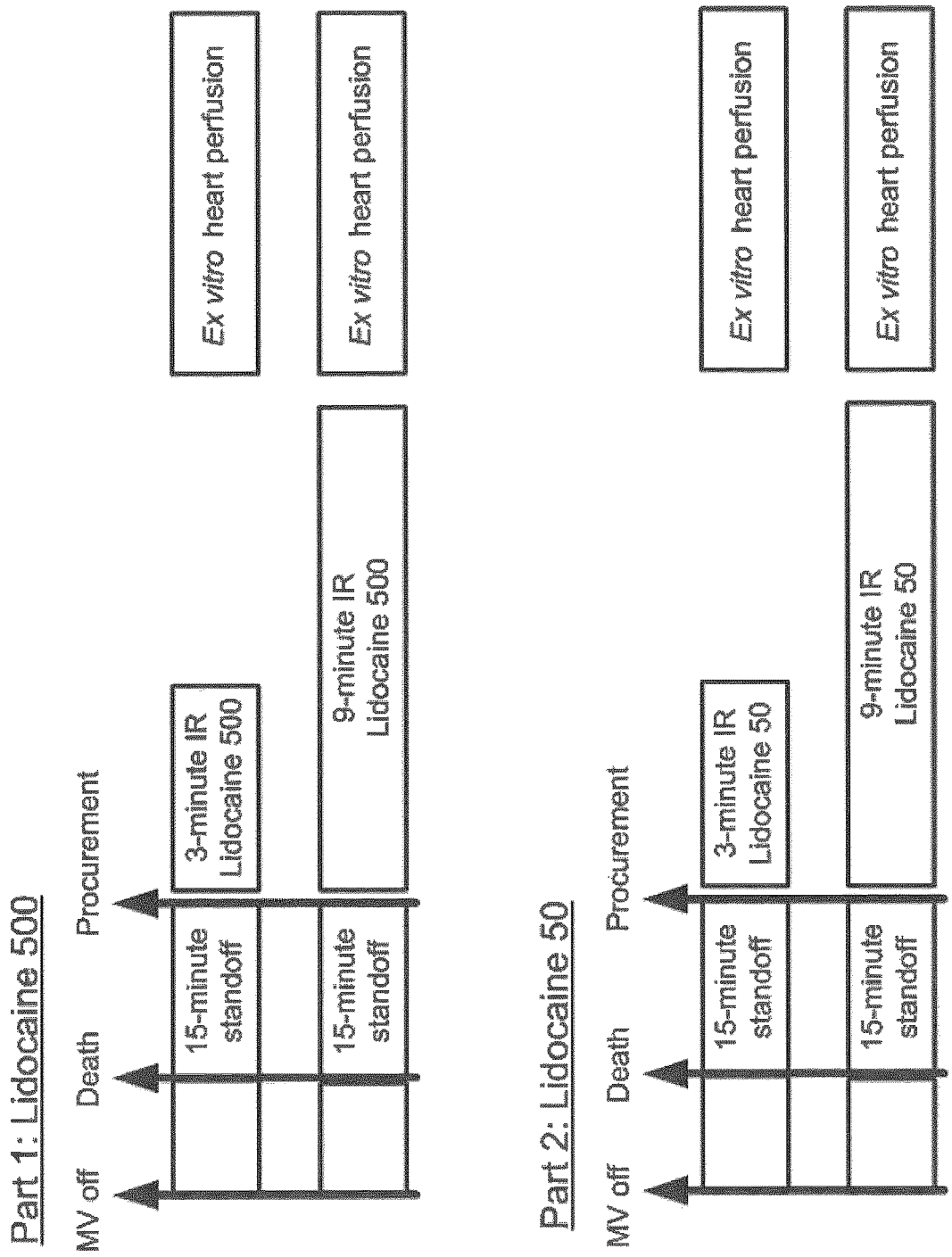
FIG. 28 is a schematic flowchart outlining the experimental protocols used in Example 4, Part 2.

Part 2: The next study assessed the effects of reducing the lidocaine concentration in the sample mildly acidic hypocalcemic oxygenated cardioplegic composition. Accordingly, this study assessed the effects of 3 minutes or 9 minutes of reperfusion with a sample mildly acidic (pH 6.9) hypocalcemic (220 µmol/L $Ca^{2+}$) oxygenated cardioplegic solution at 35° C. containing 400 µmol/L adenosine and 50 µmol/L lidocaine (FIG. 28).

The components of this sample solution are shown in TABLE IV.

TABLE IV

| Sample IV—Cardioplegic solution (pH = 6.9) | | |
|---|---|---|
| Constituent | mmol/L | IU/L |
| Adenosine | 0.4 | |
| Lidocaine | 0.05 | |
| Glucose | 10 | |
| NaCl | 123.8 | |
| KCl | 5.9 | |
| $NaHCO_3$ | 20 | |
| $NaH_2PO_4$ | 1.2 | |
| $CaCl_2$ | 0.22 | |
| $MgCl_2$ | 13 | |
| D-Mannitol | 120 | |
| Pyruvate | 1 | |
| Reduced glutathione | 3 | |
| Insulin | | 10 |

Twelve pigs were separated into two groups and then euthanized following standard protocols and medical ethics procedures following the schematic flowchart shown in FIG. 25. Immediately after procurement of each heart was completed, each heart was installed into a Quest MPS®2 Myocardial Protection System. The harvested hearts from the first group of pigs were perfused for 3 minutes with the sample mildly acidic hypocalcemic oxygenated cardioplegic composition warmed to 35° C. prior to commencing the reperfusion process for 3 minutes. The harvested hearts from the second group of pigs were perfused for 9 minutes with the sample mildly acidic hypocalcemic oxygenated cardioplegic composition that was warmed to 35° C. prior to commencing the reperfusion process.

The aortic perfusion pressure, coronary artery flow, and myocardial temperature were constantly monitored and recorded by the MPS®2 apparatus during the 3-minute or 9-minute initial reperfusion period. Blood gas samples were measured at 0, 30, 60, 120, and 180 seconds of the initial reperfusion period to collect data pertaining to changes occurring the partial pressure of $O_2$ ($PaO_2$), partial pressure of $CO_2$ ($PaCO_2$), pH levels, electrolyte levels, lactate levels among others.

After the initial 3-minute reperfusion period or the initial 9-minute reperfusion period was completed, each heart was removed from the Quest MPS®2 apparatus and transferred into an ex vivo heart perfusion (EVHP) apparatus where it was perfused with a constantly flowing supply of a blood-STEEN solution mixture (Hb 45 g/L; XVIVO Perfusion Inc., Englewood, Colo., USA) wherein its systolic function was restored and maintained in a Langendorff mode at a normothermic temperature of 35° C. for 1 hour, 3 hours, and 5 hours. The aortic pressure and heart rate were constantly monitored and processed using the LABCHART® software. At 1 hour of perfusion with the blood-STEEN solution mixture in the EVHP apparatus, each heart was transitioned from the Langendorff mode to a working mode by bringing the left atrial pressure from 0 to 8 mmHg and pacing the heart at 100 bpm. Cardiac output, coronary blood flow, aortic root, and coronary sinus blood gases were measured, and cardiac function was assessed with a pressure-volume loop catheter. After these measurements were completed, each heart was immediately returned to the Langendorff mode for an additional 2 hours, after which the measurements were repeated (i.e., 3 hours after removal from reperfusion). After these measurements were completed, each heart was immediately returned to the Langendorff mode for an additional 2 hours, after which the measurements were repeated (i.e., 5 hours after removal from reperfusion).

Figure 29:
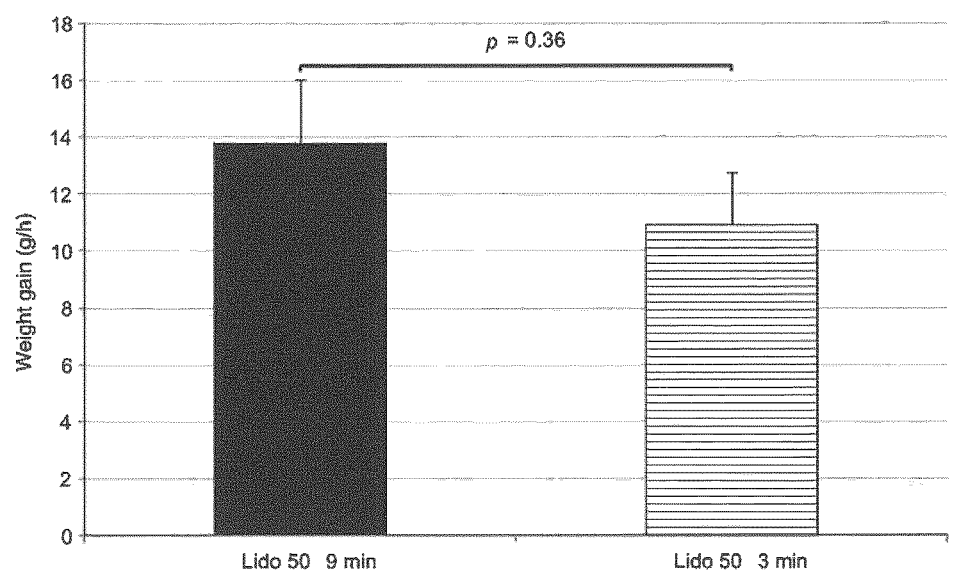
FIG. 29 is a chart showing the effect of an extended initial reperfusion with a cardioplegic reperfusate solution having a reduced concentration of anesthetic on weight gain in harvested pig hearts.

FIG. 29 shows that there were not any significant differences in myocardial edema occurring in the hearts initially reperfused for 9 minutes compared with hearts perfused for 3 minutes in the sample mildly acidic hypocalcemic oxygenated cardioplegic composition containing 400 μmol/L adenosine and 50 μmol/L lidocaine.

Figure 30:
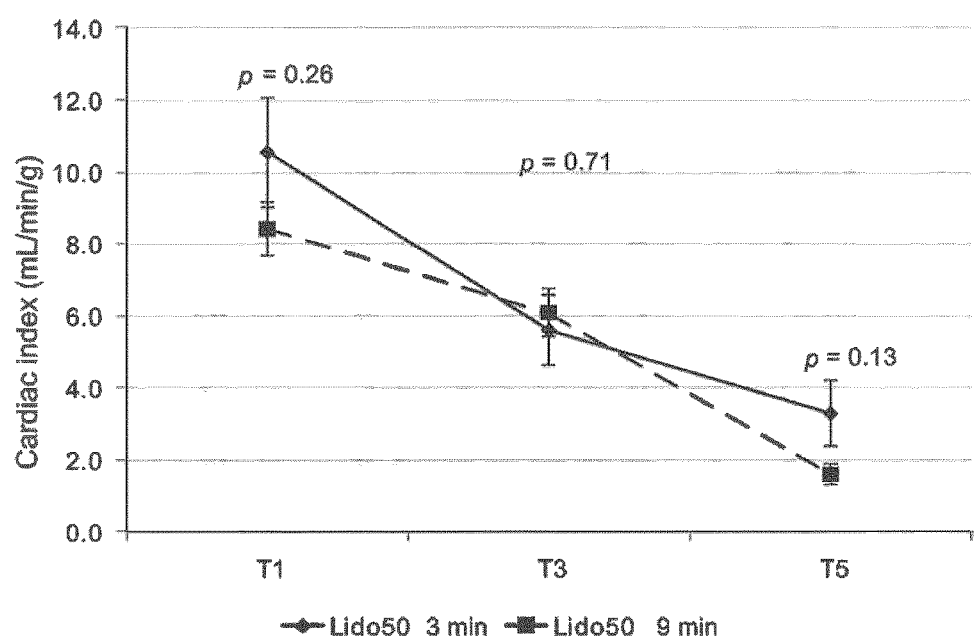
FIG. 30 is a chart showing the effect of extended initial reperfusion with a cardioplegic reperfusate solution having a reduced concentration of anesthetic on myocardial function of harvested pig hearts, measured 1 hour ("T1"), 3 hours ("T3"), and 5 hours ("T5") after harvest.

FIG. 30 shows that prolonging the initial reperfusion period from 3 minutes to 9 minutes in the sample mildly acidic hypocalcemic oxygenated cardioplegic composition containing 400 μmol/L adenosine and 50 μmol/L lidocaine, did not have detrimental effects on the functional recovery of hearts perfused for 1 hour, 3 hours, and 5 hours after reperfusion.

Figure 31:
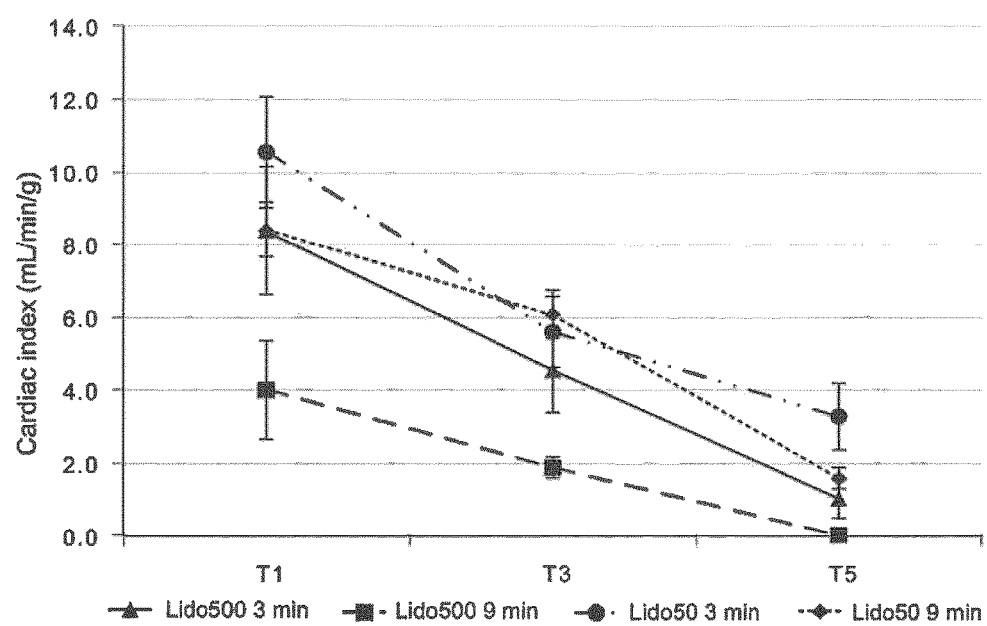
FIG. 31 is a chart showing the effect of anesthetic concentrations in cardioplegic reperfusate solutions on myocardial function of harvested pig hearts, measured 1 hour ("T1"), 3 hours ("T3"), and 5 hours ("T5") after harvest.

FIG. 31 combines myocardial functional data from Part 1 (FIG. 27) and Part 2 (FIG. 30), wherein it is apparent that the 500 μmol/L concentration of lidocaine in the cardioplegic compositions used for initial ex vivo post-harvest reperfusion has debilitating effects of donor hearts. This data also demonstrates that prolonging the initial reperfusion period beyond 3 minutes is not beneficial for restoration of homeostasis and cardiac function in harvested donor hearts.

The data presented herein indicate that a potentially effective composition for a cardioplegic solution for initial reperfusion of donor hearts is shown in TABLE IV.

It will be understood that any range of values disclosed herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Other modifications to the above-described embodiments are possible. The invention is therefore defined by the claims, which should be given a broad interpretation consistent with the description as a whole.

What is claimed is:

1. A solution comprising:
    a cardioplegia mixture comprising a calcium ion source and lidocaine; and
    a buffer for maintaining a pH of the solution,
    wherein the solution comprises 0.04 to 0.09 mmol/L of lidocaine and 0.18 to 0.26 mmol/L of calcium ion ($Ca^{2+}$), and the pH is lower than 7.4 and higher than 6.6.

2. The solution of claim 1, wherein the molar concentration of calcium ion ($Ca^{2+}$) is 0.22 mmol/L.

3. The solution of claim 1, wherein the pH is from 6.8 to 7.0.

4. The solution of claim 1, wherein the pH is 6.9.

5. The solution of claim 1, wherein the cardioplegia mixture further comprises adenosine and a magnesium ion source.

6. The solution of claim 5, comprising 0.3 to 0.45 mmol/L of adenosine, and 11 to 15 mmol/L of $Mg^{2+}$.

7. The solution of claim 1, further comprising a sodium ion source and a potassium ion source.

8. The solution of claim 7, comprising about 130 to about 160 mmol/L of $Na^+$ and 4 to 7 mmol/L of $K^+$.

9. The solution of claim 1, further comprising chloride, an osmotic buffer and a reducing agent.

10. The solution of claim 1, further comprising 70 to 180 mmol/L chloride, 8 to 12.5 mmol/L of glucose, 7.5 to 12.5 IU/L of insulin, 100 to 140 mmol/L of D-mannitol, 0.75 to 1.25 mmol/L of pyruvate, and 2.5 to 3.5 mmol/L of reduced glutathione.

11. The solution of claim 1, wherein the solution is oxygenated.

12. The solution of claim 1, comprising:
    0.3 to 0.45 mmol/L of adenosine;
    0.04 to 0.09 mmol/L of lidocaine;
    8 to 12.5 mmol/L of glucose;
    110 to 130 mmol/L of NaCl;
    4 to 7 mmol/L of KCl;
    16 to 24 mmol/L of $NaHCO_3$;
    0.9 to 1.4 mmol/L of $NaH_2PO_4$;
    0.18 to 0.26 mmol/L of $CaCl_2$;
    11 to 15 mmol/L of $MgCl_2$;
    7.5 to 12.5 IU/L of insulin;
    100 to 140 mmol/L of D-mannitol;
    0.75 to 1.25 mmol/L of pyruvate; and
    2.5 to 3.5 mmol/L of reduced glutathione.

13. The solution of claim 1, comprising:
    0.4 mmol/L of adenosine;
    0.05 mmol/L of lidocaine;
    10 mmol/L of glucose;
    123.8 mmol/L of NaCl;
    5.9 mmol/L of KCl;
    20 mmol/L of $NaHCO_3$;
    1.2 mmol/L of $NaH_2PO_4$;
    0.22 mmol/L of $CaCl_2$;
    13 mmol/L of $MgCl_2$;
    10 IU/L of insulin;
    120 mmol/L of D-mannitol;
    1 mmol/L of pyruvate; and
    3 mmol/L of reduced glutathione.

14. A method comprising reperfusing a donor heart with the solution of claim 1.

15. The method of claim 14, wherein the heart is reperfused with the solution during removal of the heart from a donor of the heart.

16. The method of claim 14, wherein the heart is reperfused with the solution in a reperfusion device.

17. The method of claim 16, wherein the heart is reperfused with the solution for at least 3 minutes immediately after removal of the heart from a donor of the heart.

18. The method of claim 14, wherein the heart is removed from a donor after circulatory death.

19. The method of claim 14, wherein the heart is at a temperature above about 25° C. and below about 37° C.

* * * * *